(12) United States Patent
Wei

(10) Patent No.: US 10,441,426 B2
(45) Date of Patent: *Oct. 15, 2019

(54) 3D PRINTING OF MESH IMPLANTS FOR BONE DELIVERY

(71) Applicant: Warsaw Orthopedic, Inc., Warsaw, IN (US)

(72) Inventor: Guobao Wei, Milltown, NJ (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/052,888

(22) Filed: Aug. 2, 2018

(65) Prior Publication Data

US 2018/0353299 A1 Dec. 13, 2018

Related U.S. Application Data

(63) Continuation of application No. 15/490,447, filed on Apr. 18, 2017, now Pat. No. 10,064,726.

(51) Int. Cl.
*A61F 2/28* (2006.01)
*A61F 2/30* (2006.01)
(Continued)

(52) U.S. Cl.
CPC .......... *A61F 2/30942* (2013.01); *A61F 2/28* (2013.01); *B29C 64/386* (2017.08); *B33Y 50/02* (2014.12); *B33Y 80/00* (2014.12); *A61F 2/2846* (2013.01); *A61F 2002/2817* (2013.01); *A61F 2002/2835* (2013.01); *A61F 2002/30588* (2013.01); *A61F 2002/30909* (2013.01);
(Continued)

(58) Field of Classification Search
CPC .. A61F 2/28; A61F 2/2846; A61F 2002/2817; A61F 2002/2835; A61F 2/30942; A61F 2002/30952; A61F 2002/30962
See application file for complete search history.

(56) References Cited

U.S. PATENT DOCUMENTS

| 4,430,760 A | 2/1984 | Smestad |
| 5,204,055 A | 4/1993 | Sachs et al. |

(Continued)

FOREIGN PATENT DOCUMENTS

| WO | 2004016438 A1 | 2/2004 |
| WO | 2014092651 A1 | 6/2014 |

(Continued)

*Primary Examiner* — Alvin J Stewart

(57) ABSTRACT

Computer implemented methods of producing a mesh implant having a compartment to enclose a bone material therein are provided. These methods include generating a 3D digital model of the mesh implant having the compartment, the 3D digital model including a virtual volume of the compartment and a virtual depth, thickness and volume of the mesh implant; generating a 3D digital model of a covering configured for closing the compartment of the mesh implant, the 3D digital model including a virtual volume of the covering for closing the compartment of the mesh implant; and instructing a 3D printer coupled to a computer to generate the mesh implant based on the 3D digital models. A computer system for making a mesh implant and a delivery system including the mesh implant are also provided.

20 Claims, 11 Drawing Sheets

(51) Int. Cl.
  *B33Y 50/02* (2015.01)
  *B33Y 80/00* (2015.01)
  *B29C 64/386* (2017.01)
  *B29L 31/00* (2006.01)
  *G06T 19/20* (2011.01)

(52) U.S. Cl.
  CPC .............. *A61F 2002/30952* (2013.01); *A61F 2002/30962* (2013.01); *A61F 2002/30985* (2013.01); *A61F 2310/00359* (2013.01); *A61F 2310/00365* (2013.01); *B29L 2031/753* (2013.01); *G06T 19/20* (2013.01); *G06T 2200/24* (2013.01)

(56) References Cited

U.S. PATENT DOCUMENTS

| | | | |
|---|---|---|---|
| 6,440,444 B2 | 8/2002 | Boyce et al. | |
| 7,832,457 B2 | 11/2010 | Calnan et al. | |
| 8,778,252 B2 | 7/2014 | Mackie et al. | |
| 8,798,780 B2 | 8/2014 | Menchik et al. | |
| 9,034,356 B2 | 5/2015 | Shimp et al. | |
| 9,101,475 B2 | 8/2015 | Wei et al. | |
| 9,220,598 B2 | 12/2015 | Betz et al. | |
| 9,277,850 B2 | 3/2016 | Kubach | |
| 9,333,082 B2 | 5/2016 | Wei et al. | |
| 9,492,278 B2 | 11/2016 | Wei et al. | |
| 10,064,726 B1 * | 9/2018 | Wei | A61F 2/30942 |
| 2001/0035886 A1 | 11/2001 | Bradshaw et al. | |
| 2005/0021142 A1 | 1/2005 | Ganz et al. | |
| 2005/0208168 A1 | 9/2005 | Hickerson et al. | |
| 2008/0042321 A1 | 2/2008 | Russell et al. | |
| 2008/0262616 A1 | 10/2008 | McKay | |
| 2010/0049322 A1 | 2/2010 | McKay | |
| 2011/0054408 A1 | 3/2011 | Wei et al. | |
| 2012/0165969 A1 | 6/2012 | Elsey | |
| 2014/0191439 A1 | 7/2014 | Davis | |
| 2014/0212471 A1 | 7/2014 | Drapeau et al. | |
| 2014/0236299 A1 | 8/2014 | Roeder et al. | |
| 2015/0054195 A1 | 2/2015 | Greyf | |
| 2015/0259548 A1 | 9/2015 | Wang et al. | |
| 2016/0038207 A1 | 2/2016 | Wei et al. | |
| 2016/0250038 A1 | 9/2016 | Wei et al. | |

FOREIGN PATENT DOCUMENTS

| | | |
|---|---|---|
| WO | 2015167520 A1 | 11/2015 |
| WO | 2016085907 A1 | 6/2016 |

* cited by examiner

3D PRINTING OF MESH IMPLANTS FOR BONE DELIVERY

BACKGROUND

Three-dimensional (3D) printing is an additive printing process used to make three-dimensional solid objects from a digital model. 3D printing techniques are considered additive processes because they involve the application of successive layers of material to make the object being printed.

3D printing technology is applied in various industries for manufacturing and planning. For example, the automotive, aerospace and consumer goods industries use 3D printing to create prototypes of parts and products 3D printing has also been used in the architectural industry for printing structural models. The applications of 3D printing in private and government defense have grown rapidly as well.

3D printing has had a significant impact in the medical field. Medical applications of 3D printing have been used to produce dental implants and prosthetics. 3D printing has also been used in the fabrication of drug delivery devices. A variety of drug delivery devices may be created which allow for customizable drug release profiles.

Traditional 3D printing allows an object to be created by depositing a material over a flat fabrication platform one layer at a time. Once a first layer is deposited, a second layer is deposited on top of the first layer. The process is repeated as necessary to create a multi-layered solid object. However, 3D printing does not allow for continuous extrusion to create an object.

Bone defects may be caused by a number of different factors, including but not limited to trauma, pathological disease or surgical intervention. Because bone provides both stability and protection to an organism, these defects can be problematic. In order to address these defects, compositions that contain both natural and synthetic materials have been developed. These compositions may, depending upon the materials contained within them, be used to repair tissues and to impart desirable biological and/or mechanical properties to the bone defect.

Among the known bone repair materials and bone void fillers is autologous cancellous bone. This type of bone has the advantage of being both osteoinductive and non-immunogenic. Unfortunately, this type of bone is not available under all circumstances. Moreover, donor site morbidity and trauma add to the limitations of autologous cancellous bone. One alternative to autologous bone is allograft bone. Unfortunately, allograft bone has a lower osteogenic capacity than autograft bone, has a high resorption rate, creates less revascularization at the bone defect site, typically induces a greater immunogenic response and may result in the transfer of certain diseases.

In order to avoid the issues that attach to the use of autologous and allograft bone, one may use synthetic materials. However, known synthetic materials suffer from one or more of the following drawbacks, including unacceptable workability, handling and setting parameters, insufficient density; undesirable absorption rates; and an inability to impart adequate stability.

Generally, bone tissue regeneration is achieved by filling a bone repair site with a bone graft. Over time, the bone graft is incorporated by the host and new bone remodels the bone graft. In order to administer the bone graft, it is common to use a monolithic bone graft or to form an osteoimplant comprising particulated bone in a carrier. The carrier is thus chosen to be biocompatible, to be resorbable, and to have release characteristics such that the bone graft is accessible. Ordinarily, the formed implant, whether monolithic or particulated and in a carrier, is substantially solid at the time of implantation and thus does not conform to the implant site. Further, the implant is substantially complete at the time of implantation and thus provides little ability for customization, for example, by the addition of autograft.

Traditional methods of 3D printing do not allow for a printed mesh implant having one or more compartments to be filled with bone material and then after filling the one or more compartments with bone material, a cover is printed on the mesh implant. Thus, there is a need for a computer implemented method of producing a mesh implant having a hollow compartment, which can be filled with bone material for delivery at an intended bone repair site. There is also need for a computer system that can be used to implement the steps required to produce the mesh implant having a compartment that can be filled with bone material.

SUMMARY

Provided are computer implemented methods of producing a mesh implant having a compartment to enclose a bone material within the mesh implant. The computer implemented methods comprise generating a 3D digital model of the mesh implant having the compartment, the 3D digital model including a virtual volume of the compartment to enclose the bone material therein and a virtual depth, thickness and volume of the mesh implant; generating a 3D digital model of a covering configured for closing the compartment of the mesh implant, the 3D digital model including a virtual volume of the covering for closing the compartment of the mesh implant and a virtual depth and thickness of the covering for closing the compartment of the mesh implant; instructing a 3D printer coupled to a computer to generate the mesh implant based on the 3D digital model of the mesh implant; filling the compartment of the mesh implant with an amount of the bone material; and instructing the 3D printer to generate the covering based on the 3D digital model of the covering for enclosing the bone material within the compartment of the mesh implant. According to one aspect, the resulting mesh implant is seamless and/or corner-less.

According to another aspect, the bone material enclosed within the compartment of the mesh implant or bag can include autograft, allograft, demineralized bone matrix fiber, demineralized bone chips or a combination thereof. In other embodiments, the bone material enclosed within the compartment of the mesh implant or bag can include (i) fully demineralized bone fibers and surface demineralized bone chips; (ii) the fully demineralized bone fibers and surface demineralized bone chips form a demineralized bone matrix; or (iii) a demineralized bone matrix material comprising fully demineralized bone matrix fibers and surface demineralized bone chips in a ratio of from about 25:75 to about 75:25.

According to various aspects, the mesh implant can include a bioactive agent, the bioactive agent including protein, carbohydrates, lipids, collagen, allograft bone, autograft bone, tricalcium phosphate, hydroxyapatite, growth and differentiation factors, carriers for growth factors, growth factor extracts of tissues, demineralized bone matrix, bone marrow aspirate, concentrates of lipid derived or marrow derived adult stem cells, umbilical cord derived stem cells, committed or partially committed cells from the osteogenic or chondrogenic lineage, antimicrobials, antibiotics, statins or combinations thereof.

Provided is a computer system for making a mesh implant having a compartment to enclose a bone material within the mesh implant, the computer system comprising logic encoded in the computer for (i) generating a 3D digital model of the mesh implant having the compartment, the 3D digital model including a virtual volume of the compartment to enclose the bone material therein and a virtual depth, thickness and volume of the mesh implant; (ii) generating a 3D digital model of a covering configured for closing the compartment of the mesh implant, the 3D digital model including a virtual volume of the covering for closing the compartment of the mesh implant and a virtual depth and thickness of the covering for closing the compartment of the mesh implant, (iii) instructing a 3D printer coupled to the computer system to generate the mesh implant based on the 3D digital model of the mesh implant; (iv) filling the compartment of the mesh implant with an amount of the bone material; and (v) instructing the 3D printer to generate the covering based on the 3D digital model of the covering for enclosing the bone material within the compartment of the mesh implant.

According to other aspects, a delivery system including a seamless mesh implant having a compartment for enclosing bone material therein is also provided. The seamless mesh implant or bag can be made by using a 3D printer coupled to a computer, the computer programmed for (i) generating a 3D digital model of the mesh implant having the compartment, the 3D digital model including a virtual volume of the compartment to enclose the bone material therein and a virtual depth, thickness and volume of the mesh implant; (ii) generating a 3D digital model of a covering configured for closing the compartment of the mesh implant, the 3D digital model including a virtual volume of the covering for closing the compartment of the mesh implant and a virtual depth and thickness of the covering for closing the compartment of the mesh implant; (iii) instructing a 3D printer coupled to the computer system to generate the mesh implant based on the 3D digital model of the mesh implant; (iv) filling the compartment of the mesh implant with an amount of the bone material, and (v) instructing the 3D printer to generate the covering based on the 3D digital model of the covering for enclosing the bone material within the compartment of the mesh implant. In various embodiments, the mesh implant is biodegradable.

According to yet another aspect, provided is a computer implemented method for creating hollow structures, the method comprising inputting instructions to direct a processor, the processor configured to induce rotation of a print surface in alternating clockwise and counterclockwise directions, and ejection of material from a print head to the print surface to make a strand having a wave-like pattern with alternating peaks and crests, and rotating the print head such an angular distance to create a plurality of interconnected strands on the print surface.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent regarding the following description, appended claims and accompanying drawings.

Figure 1:
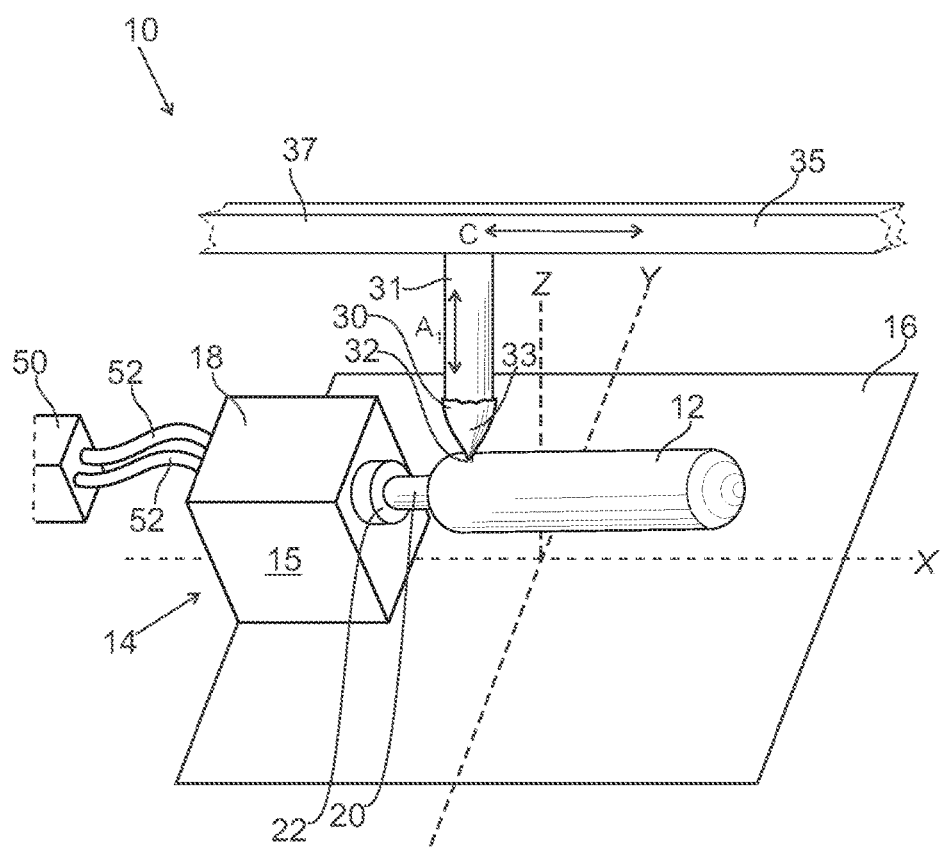
FIG. 1 illustrates a perspective view of an exemplary 3D printing device according to an aspect of the present application. The 3D printing device includes a rotatable printing surface to facilitate continuous extrusion of a predetermined hollow implant.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in *Pharmaceutical Substances: Syntheses, Patents, Applications* by Axel Kleemann and Jurgen Engel, Thieme Medical Publishing, 1999; *Merck Index: An Encyclopedia of Chemicals, Drugs, and Biologicals*, edited by Susan Budavari et al., CRC Press, 1996; and *United States Pharmacopeia-25/National Formulary-20*, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Demineralized, as used herein, refers to any material generated by removing mineral material from tissue, for example, bone tissue. In certain embodiments, demineralized bone material may be added to the bone void filler. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure in some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone void filler can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000-1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are demineralized, however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

The bone implant devices and methods provided enhance bone growth by reducing the gaps that may exist between the DBM particles and reduce the distance for cells (for example, osteoclasts, osteoblasts, etc.) to travel throughout the device to allow those cells to receive an adequate osteoinductive signal as opposed to only along the surface of the device. In some embodiment, the device improves the fusion of adjacent interspinous processes.

According to one aspect, there is a 3D printed bone graft delivery device comprising: a porous biodegradable graft body for inducing bone growth at a surgical site, the porous biodegradable graft body having demineralized bone matrix (DBM) fibers disposed within the porous biodegradable body, wherein the porous biodegradable graft body facilitates transfer of cells into and out of the porous biodegradable graft body to induce bone growth at the surgical site.

3D Printer Device

Provided is 3D printing devices and methods of use for creating hollow structures such as mesh implants or bags. Also provided are 3D printing devices including a rotatable printing surface to create such hollow structures. Further provided are devices and methods for 3D printing onto a rotatable printing surface by continuous extrusion instead of stratified layers. Additionally, provided are devices and methods for creating structures having a meshed design that are strong, flexible, stretchable and biocompatible.

Turning now to FIGS. 1-7, provided is a 3D printing device 10 for fabricating hollow structures, such as mesh bags 70. 3D printing is typically done in 2 dimensions, one layer at a time. Material is laid out on a flat surface and the three-dimensional structures are built up one layer at a time, usually through a melting or sintering process. In some embodiments, a 3D printer having a rotatable printing surface is provided to allow printing hollow structures, such as, for example, mesh bags. In some embodiments, a print head applies material to the print surface through continuous extrusion instead of stratified layers, as is done by traditional 3D printing devices. In some embodiments, the 3D printing device creates stronger structures and generates less waste than traditional 3D printing devices.

As shown in FIG. 1, provided is a 3D printing device 10 for use in the fabrication of mesh bags 70. 3D printing device 10 includes a table 14 having a base 16 and a printing surface 12. In some embodiments, printing surface 12 is mounted onto table 14 including base 16. Base 16 is configured for planar movement. In some embodiments, base 16 is movable in the x-y plane and is laterally movable in both the x axis and the y axis for precise positioning of printing surface 12. Printing surface 12, in some embodiments, is fixedly disposed with table 14 such that lateral movement of base 16 causes lateral movement of printing surface 12. Movement of base 16 allows for positioning of printing surface 12 relative to print head 30 to facilitate depositing materials onto printing surface 12, as discussed herein.

Figure 2:
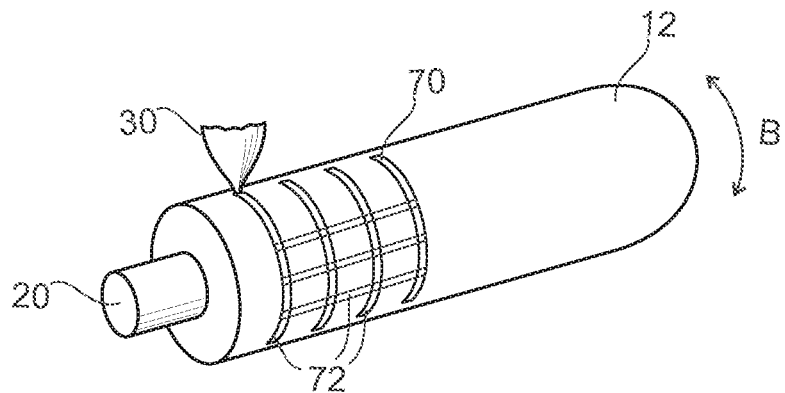
FIG. 2 illustrates a perspective view of components of an exemplary 3D printing device according to an aspect of the present application. Specifically, shown is a printing surface having a cylindrical shape configured to create a cylindrically shaped hollow structure, such as a mesh bag. The printing surface is adjacent to and/or contacts a print head.
Figure 3:
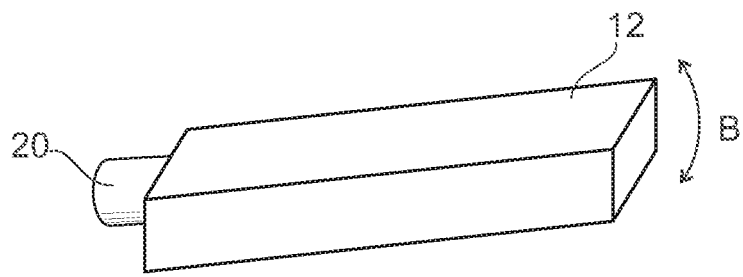
FIG. 3 illustrates a perspective view of components of an exemplary 3D printing device according to an aspect of the present application. Specifically, shown is a printing surface having a rectangular cross-section configured to create a rectangular or square shaped hollow structure, such as a mesh bag.
Figure 4:
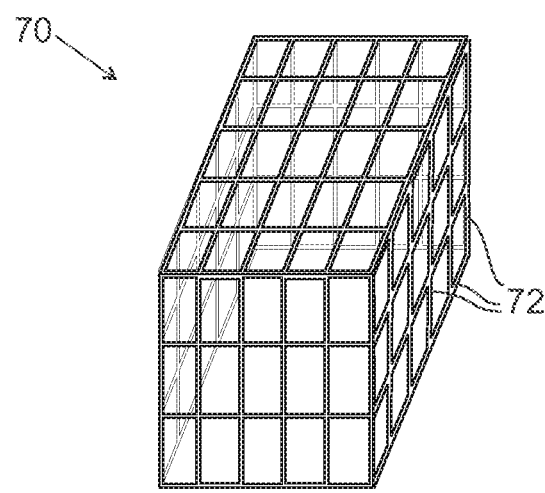
FIG. 4 illustrates a perspective view of an exemplary hollow structure created through use of a 3D printing device, according to an aspect of the present application. The depicted hollow structure includes a rectangular cross section.

Printing surface 12 is rotatable about an axis of rotation, as shown in FIGS. 2 and 3. In some embodiments, rotating printing surface 12 includes a cylindrical shape extending along a longitudinal axis, as shown in FIG. 2. This allows printing of a round or circular implant with a hollow region as the implant takes on the shape of the printing surface 12. In some embodiments, the printing surface 12 includes other cross-sectional shapes, such as, for example, rectangular, oval, polygonal, irregular, undulating, or lobed. For example, as shown in FIG. 3, printing surface 12 may have a rectangular cross-section extending along a longitudinal axis. This allows printing of a square or rectangular implant, as the print surface rotates, the implant will take the shape of the print surface. In alternative embodiments, printing surface 12 includes a uniform diameter and/or cross-section along its entire length. In other embodiments, printing surface 12 includes a changing diameter or cross-section along its length. For example, in some embodiments the diameter may increase from one end of printing surface 12 to the other. In some embodiments, the cross section of printing surface 12 changes from one end to the other. For example, one end of printing surface 12 may have a circular cross-section while the opposite end may have a rectangular cross-section. The size and shape of printing surface 12 may be changed according to the specifications and needs of a particular medical procedure. In some embodiments, mesh bags are printed onto the printing surface into which another object, such as for example, bone material (e.g. surface demineralized bone chips and fully demineralized bone fibers), can be placed inside the hollow region or compartment. The shape of printing surface 12 defines the shape of the hollow structure created. As shown in FIG. 2, the shape of the mesh implant or bag 70 created is cylindrical. As shown in FIG. 4, the shape of the mesh implant or bag 70 created is that of a hollowed out rectangular prism.

Printing surface 12 is rotatable about a rotation of an axis defined by extension shaft 20, as discussed herein. In various embodiments, printing surface 12 is rotatable in both clockwise and counterclockwise directions, as shown by arrow B in FIGS. 2 and 3. Printing surface 12 is configured to change direction of rotation multiple times throughout the course of fabrication of a hollow structure, such as, for example, mesh implant or bag 70, as discussed herein. For example, printing surface 12 can rotate along a rotational axis 360 degrees clockwise and/or counterclockwise to print the implant.

In some embodiments, printing surface 12 is movable between an expanded configuration and a collapsed configuration. In some embodiments, material 40 (which can be a biodegradable polymer) is deposited onto printing surface 12 while in the expanded configuration, and printing surface 12 is moved to the collapsed configuration to remove the printed hollow structure. The print head 30 can contact the printing surface 12 or there can be a gap between the printing surface 12 and the print head 30 so that the material can be printed on the printing surface 12.

In some embodiments, printing surface 12 is fixedly disposed with table 14 via a mounting bracket 18. The mounting bracket 18 may include covering 15 for protection. In some embodiments, mounting bracket 18 includes a motor to provide a rotational force to move printing surface 12. In some embodiments, mounting bracket 18 is connected to extension shaft 20. Printing surface 12 is connected to extension shaft 20 at a first end of printing surface 12. Extension shaft 20 defines an axis of rotation for printing surface 12 and is connected to mounting bracket 18 via a collet 22. In some embodiments, collet 22 is expandable to loosen the grip on extension shaft 20. This allows extension shaft 20 and printing surface 12 to be changed out for another printing surface 12 which may be sized and/or shaped differently to cater to the needs of a particular procedure.

In some embodiments, the 3D printing device further includes a print head 30, such as, for example, an applicator that is movable in a direction transverse to the plane of movement for the base 16. In some embodiments, print head 30 is movable in the z axis, as shown by A1 in FIG. 1, to allow for different size fixtures, variable surface structures and to control the thickness of the extruded layer. Thus, print head 30 is movable to have an adjustable distance from printing surface 12. Additionally, print head 30 is movable to accommodate printing surfaces having various diameters or printing surfaces having gradient diameters. In some embodiments, print head 30 is also movable in the x and y planes parallel with the plane of movement for base 16. Thus, in some embodiments, print head 30 is movable in an opposite direction from the movement of printing surface 12 to facilitate faster printing. In some embodiments, print head 30 is suspended from a track 35. Track 35 provides a base of support for print head 30. In some embodiments, track 35 provides a predefined route of allowable movement for print head 30 in directions shown as C. In some embodiments, track 35 is hollow to allow flow of material 40 to be delivered to printing surface 12, as described herein.

In some embodiments, printing surface 12 is treated with an adhesive material. The adhesive material may be textured or coated onto printing surface 12. The adhesive may be heat sensitive or heat activated such that printing surface 12 becomes adhesive to material 40 when printing surface 12 is heated, as discussed herein. An adhesive coating aids in preventing printed material 40 from falling off printing surface 12 during rotation. In some embodiments, the adhesive is deactivated through cooling. In some embodiments, the adhesive may be removed by placing printing surface 12 in a solvent to dissolve the adhesive material. Once the adhesive material is removed, a hollow structure printed to printing surface 12 may be removed.

Figure 6:
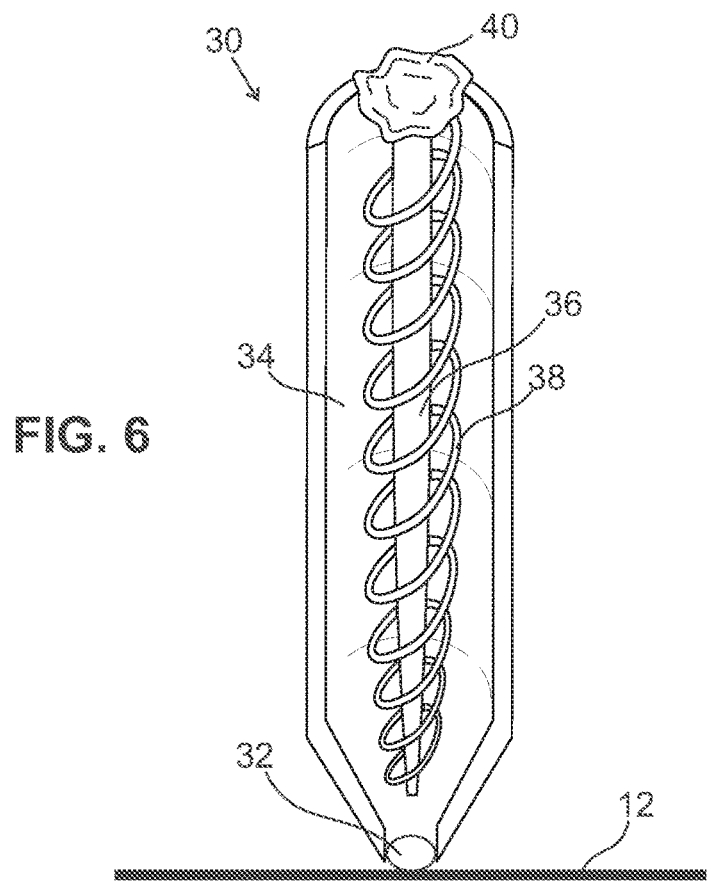
FIG. 6 illustrates a side view of components of an exemplary 3D printing device according to an aspect of the present application. Specifically, shown is a print head which processes material to be extruded to the printing surface.

As shown in FIGS. 1 and 6, print head 30 includes a distal opening 32 through which material 40 is deposited on printing surface 12. A tube portion 31 of print head 30 includes a first diameter and extends distally to a head portion 33 having a second diameter. In some embodiments, the second diameter is smaller than the first diameter. In various embodiments, material 40 includes a biodegradable polymer. In some embodiments, material 40 comprises a bioerodible, a bioabsorbable, and/or a biodegradable biopolymer. Examples of suitable biopolymers include but are not limited to poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA poloxamer 407. PEG-PLGA-PEG triblock copolymers, SAIB (sucrose acetate isobutyrate) or combinations thereof. In various embodiments, material 40 comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

Print head 30 includes an inner lumen 34 and a central feed shaft 36 as illustrated in FIG. 6. Feed shaft 36 is configured to turn feed threads 38 to feed material 40 from the proximal end of print head 30 through distal opening 32. Material 40 is maintained in an external reservoir (not shown) and fed into lumen 34. In some embodiments, material 40 is driven into lumen 34 by gravity. In some embodiments, material 40 is drawn into lumen 34 by turning feed shaft 36 and feed threads 38. In some embodiments, 3D printing device 10 includes multiple print heads 30, each configured to deposit material 40 onto printing surface 12.

In some embodiments, as illustrated in FIG. 1, 3D printing device 10 further includes a temperature control unit 50 such as, for example, a heating or cooling unit connected to printing surface 12. In some embodiments, temperature control unit 50 includes a heating unit. In other embodiments, temperature control unit 50 includes a cooling unit. In some embodiments, temperature control unit 50 is used to heat printing surface 12 through electric heating elements underneath the surface of printing surface 12. Sufficient energy may be supplied through such electric conduits to provide a temperature on the surface of printing surface 12 to melt and bond material 40 applied from print head 30. In such an embodiment, as illustrated in FIG. 1, conduits 52 are electric heating conduits. In some embodiments, where material 40 comprises a highly viscous material, a heated printing surface 12 allows material 40 to flow. In other embodiments, material 40 is heated or cooled in a reservoir 37 to allow the desired flowability or viscosity of material 40 to make the implant.

In some embodiments, temperature control unit 50 comprises a cooling unit. The cooling unit is used to cool printing surface 12 through refrigerant supply and return lines underneath printing surface 12. In such an embodiment, the supply and return lines are conduits 52. The conduits 52 supply cooling fluid to printing surface 12 to cool and solidify hot material 40 extruded onto the surface. In alternative embodiments, reservoir 37 can have the cooling and heating unit to allow cooling or heating of the material.

Figure 7:
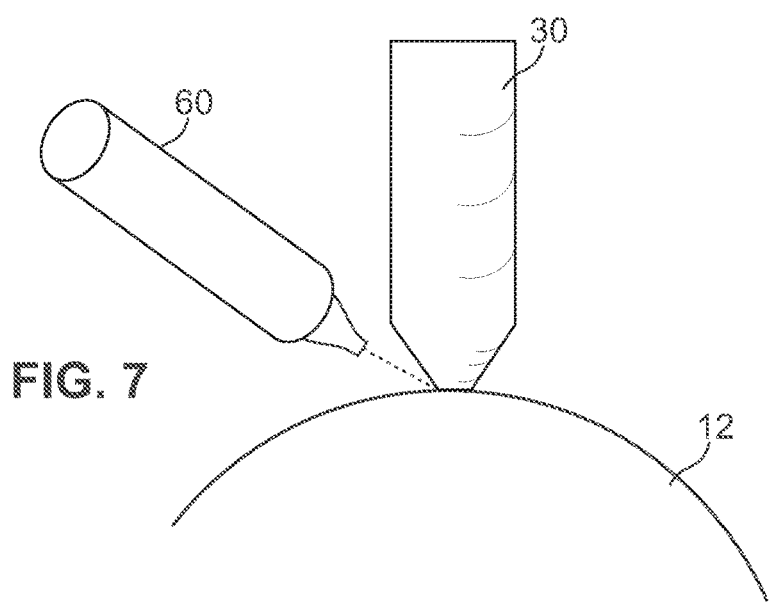
FIG. 7 illustrates a side view of components of an exemplary 3D printing device according to an aspect of the present application. Specifically, shown is a radiation source, such as, for example, a laser mounted adjacent the print head to apply an energy to sinter or melt the material discharged from the print head.

According to some aspects, 3D printing device 10 includes a radiation source configured to supply and transfer energy to at least a portion of powdered material 40 (e.g., polymer material) applied to the surface. In some embodiments, the radiation source is a laser 60 positioned adjacent print head 30. Laser 60 articulates such that the supplied beam can be focused on selected portions of printing surface 12. As shown in FIG. 7, laser 60 is configured to be used during or after print head 30 deposits material 40 (e.g., polymer material) onto printing surface 12. The beam of laser 60 is focused onto portions of material 40 on printing surface 12 to melt or sinter material 40 as desired. Once the printed hollow structure is complete, it may be removed from the residual powdered material 40 left on printing surface 12, or the residual powdered material 40 is brushed away. In some embodiments, the laser is focused at a point adjacent distal opening 32 to sinter material 40 as it is deposited onto printing surface 12. Such embodiments may facilitate the elimination of waste since most of material 40 extruded onto printing surface 12 is sintered.

In some embodiments, laser 60 may include any wavelength of visible light or UV light. In some embodiments, laser 60 emits alternative forms of radiation, such as, for example, microwave, ultrasound or radio frequency radiation. In some embodiments, laser 60 is configured to be focused on a portion of printing surface 12 to sinter material 40 deposited thereon. Laser 60 may be emitted in a beam having a small diameter. For example, the diameter of the beam may be between about 0.01 mm and about 0.8 mm. In some embodiments, the diameter of the beam may be between about 0.1 mm and about 0.4 mm. In some embodiments, the diameter of the beam is adjustable to customize the intensity of the sintering. In some embodiments, material 40 is deposited on the printing surface 12 and print head 30 removes by, for example, heating material 40 to remove unwanted material 40 from printing surface 12 to make the implant. Material 40 that is remaining on the printing surface 12 after removal of the unwanted material 40 will be the implant.

Figure 8:
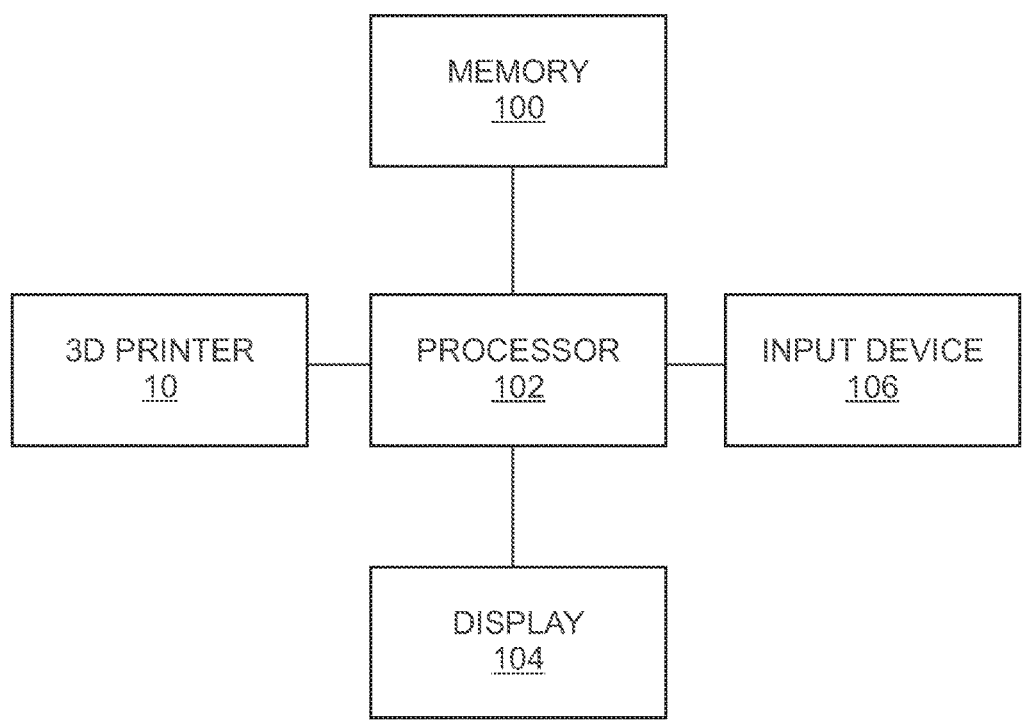
FIG. 8 illustrates an embodiment of a computer-implemented system for producing a hollow structure, such as a mesh bag.

In other aspects, as illustrated in FIG. 8, 3D printing device 10 includes a controller or processor 102 to accept instructions and automatically manufacture a hollow structure, such as, for example, a mesh implant or bag 70, based on the instructions. In some embodiments, processor 102 comprises memory 100 for temporary or permanent storage of instructions. Various instructions may be programmed and stored in memory 100 to make multiple designs of mesh bags and/or mesh covers for the mesh bags in some embodiments, 3D printing device 10 includes an input device 106, such as, for example, a keyboard to input commands and instructions. In some embodiments, processor 102 of 3D printing device 10 is configured to receive commands and instructions from an external computer. For example, various instructions may be stored and executed locally on an external computer to operate 3D printing device 10. In some embodiments, the computer and the 3D printing device can be one single device with component parts.

In some embodiments, processor 102 comprises logic to execute one or more instructions to carry out instructions of the computer system (for example, transmit instructions to the 3D printer, etc.). The logic for executing instructions may be encoded in one or more tangible media for execution by processor 102. For example, processor 102 may execute codes stored in a computer-readable medium such as memory 100. The computer-readable medium may be stored in, for example, electronic (for example, RAM (random access memory), ROM (read-only memory), EPROM (erasable programmable read-only memory), magnetic, optical (for example, CD (compact disc), DVD (digital video disc)), electromagnetic, semiconductor technology, or any other suitable medium.

In some embodiments, the instructions include dimensions of a mesh bag to be made. For example, the instructions may include programming as to the length and thickness of the mesh bag. Processor 102 carries out the instructions by causing movement of base 16 relative to print head 30 while material 40 is applied to printing surface 12. Additionally, processor 102 may cause movement of print head 30 in a direction away from printing surface 12 to allow for a thicker layer of material 40, according to the predetermined specifications in the instructions. In some embodiments, processor 102 is configured to provide a single layer of material to make the mesh bag. The layer of material 40 deposited onto printing surface 12 may have uniform thicknesses or may include varied thicknesses, such as thickness gradients across the length of the mesh bag. In some embodiments, the dimensions of the mesh implant or bag 70 may range from about 1 cm to about 1 meter in length, or from about 3 cm to about 8 cm in length, or from about 2 mm to about 30 mm in thickness, or from about 2 mm to about 10 mm in thickness, or from about 2 mm to about 30 mm in width, or from about 2 mm to about 10 mm in width.

Once processor 102 receives the instructions, processor 102 directs 3D printing device 10 to make the mesh bag based on the received instructions. In some embodiments, processor 102 directs the lateral movement of base 16 and printing surface 12, and the movement of print head 30 transverse to base 16 and printing surface 12. In some embodiments, processor 102 also controls the direction of rotation, the degree of rotation and the speed of rotation of printing surface 12. In some embodiments, processor 102 moves, focuses and directs the laser 60 to emit radiation at a predetermined point on printing surface 12. In some embodiments, processor 102 directs temperature control unit 50 to heat or cool printing surface 12. Based on the instructions received, processor 102 coordinates simultaneous and/or ordered movement of base 16, printing surface 12, and print head 30 relative to one another. Processor 102 also controls the application of material 40 onto printing surface 12. For example, processor 102 directs the pressure at which material 40 is released onto printing surface 12. Processor 102 also directs the patterns of application onto printing surface 12, including portions where material 40 is not applied to printing surface 12 to reduce waste. Processor 102 may also direct laser 60 to emit radiation, such as for example, focused beams of light, in controlled pulses to sinter preselected portions of material 40 on printing surface 12.

In some embodiments, processor 102 directs motors which control the movement and rotation of at least base 16, printing surface 12, and print head 30 relative to one another. In some embodiments, processor 102 directs coarse and/or fine movement of components of 3D printing device 10.

Although the components of the system of FIG. 8 are shown as separate, they may be combined in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc) as required for the particular implementation of the embodiments disclosed. Indeed, even a single general purpose computer (or other processor-controlled device) executing a program stored on an article of manufacture (for example, recording medium or other memory units) to produce the functionality referred to herein may be utilized to implement the illustrated embodiments. It also will be understood that the plurality of computers or servers can be used to allow the system to be a network based system having a plurality of computers linked to each other over the network, Internet, Wi-Fi or the plurality of computers can be connected to each other to transmit, edit, and receive data via cloud computers or in a data drop box.

The computer (for example, memory, processor, storage component, etc.) may be accessed by authorized users. Authorized users may include at least one engineer, technician, surgeon, physician, nurse, and/or health care provider, manufacturer, etc.

The user can interface with the computer via a user interface that may include one or more display devices 104 (for example, CRT, LCD, or other known displays) or other output devices (for example, printer, etc.), and one or more input devices (for example, keyboard, mouse, stylus, touch screen interface, or other known input mechanisms) for facilitating interaction of a user with the system via user interface. The user interface may be directly coupled to a database or directly coupled to a network server system via the Internet or cloud computing. In accordance with one embodiment, one or more user interfaces are provided as part of (or in conjunction with) the illustrated systems to permit users to interact with the systems.

The user interface device may be implemented as a graphical user interface (GUI) containing a display 104 or the like, or may be a link to other user input/output devices known in the art. Individual ones of a plurality of devices (for example, network/stand-alone computers, personal digital assistants (PDAs), WebTV (or other Internet-only) terminals, set-top boxes, cellular phones, screen phones, pagers, blackberry, smart phones, iPhone, iPad, table, peer/non-peer technologies, kiosks, or other known (wired or wireless) communication devices, etc.) may similarly be used to execute one or more computer programs (for example, universal Internet browser programs, dedicated interface programs, etc.) to allow users to interface with the systems in the manner described. Database hardware and software can be developed for access by users through personal computers, mainframes, and other processor-based devices. Users may access data stored locally on hard drives. CD-ROMs, stored on network storage devices through a local area network, or stored on remote database systems through one or more disparate network paths (for example, the Internet).

The database can be stored in storage devices or systems (for example, Random Access Memory (RAM), Read Only Memory (ROM), hard disk drive (HDD), floppy drive, zip drive, compact disk-ROM, DVD, bubble memory, flash drive, redundant array of independent disks (RAID), network accessible storage (NAS) systems, storage area network (SAN) systems, etc.). CAS (content addressed storage) may also be one or more memory devices embedded within a CPU, or shared with one or more of the other components, and may be deployed locally or remotely relative to one or more components interacting with the memory or one or more modules. The database may include data storage device, a collection component for collecting information from users or other computers into a centralized database, a tracking component for tracking information received and entered, a search component to search information in the database or other databases, a receiving component to receive a specific query from a user interface, and an accessing component to access the centralized database. A receiving component is programmed for receiving a specific query from one of a plurality of users. The database may also include a processing component for searching and processing received queries against a data storage device containing a variety of information collected by a collection device.

The disclosed system may, in some embodiments, be a computer network based system. The computer network may take any wired/wireless form of known connective technology (for example, corporate or individual LAN, enterprise WAN, intranet, Internet, Wi-Fi, Virtual Private Network (VPN), combinations of network systems, etc.) to allow a server to provide local/remote information and control data to/from other locations (for example, other remote database servers, remote databases, network servers/user interfaces, etc.). In accordance with one embodiment, a network server may be serving one or more users over a collection of remote and disparate networks (for example, Internet, intranet, VPN, cable, special high-speed ISDN lines, etc.). The network may comprise one or more interfaces (for example, cards, adapters, ports) for receiving data, transmitting data to other network devices, and forwarding received data to internal components of the system (for example, 3D printers, printer heads, etc.).

In accordance with one embodiment of the present application, the data may be downloaded in one or more textual/graphical formats (for example, RTF, PDF, TIFF, JPEG, STL, XML, XDFL, TXT etc.), or set for alternative delivery to one or more specified locations (for example, via e-mail, etc.) in any desired format (for example, print, storage on electronic media and/or computer readable storage media such as CD-ROM, etc.). The user may view the search results and underlying documents at the user interface, which allows viewing of one or more documents on the same display 104.

Mesh Formulations

In some embodiments, mesh bags 70 are formed from material 40 extruded from print head 30. Mesh bags 70 comprise a system of threads 72 which are extruded directly onto printing surface 12. Threads 72 may be extruded in various patterns, and may be sized according to the requirements of a particular application. For example, threads 72 may be extruded from print head 30 in a weave pattern in which threads 72 are interwoven with one another such that each thread 72 alternatingly interlaces above and below adjacent threads 72. In other embodiments, threads 72 may be extruded in other ways. For example, horizontal rows of threads 72 may be extruded in a first step, and in a second step vertical rows of threads 72 may be extruded on top of the horizontal rows. A radiation source, such as laser 60 may be configured to sinter the extruded rows together to form a mesh implant or bag 70.

Figure 5:
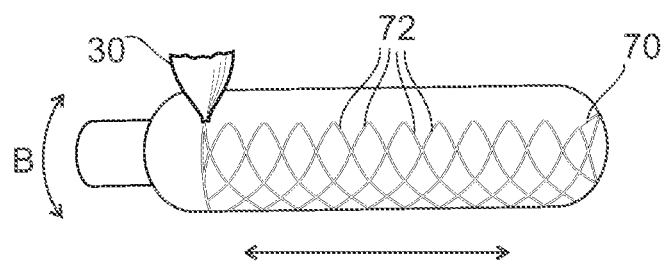
FIG. 5 illustrates a perspective view of components of an exemplary 3D printing device according to an aspect of the present application. Specifically, shown is the movement of a printing surface while a print head, such as, for example, an applicator continuously extrudes material to the surface to form a mesh pattern.
Figure 5A:
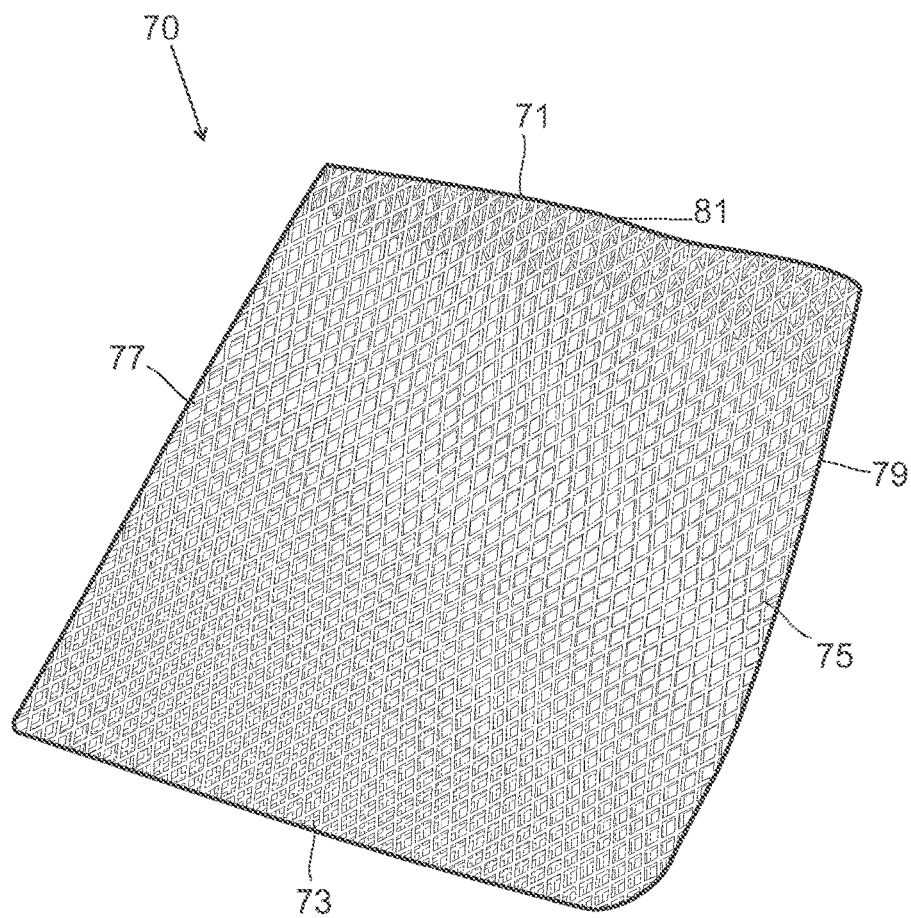
FIG. 5A illustrates a perspective view of a mesh bag having a hollow interior region formed from a 3D printing device according to an aspect of the present application.

In some embodiments as shown in FIG. 5A, a completely printed mesh implant or bag 70 is formed having a continuous surface 75 formed from threads 72. Mesh implant or bag 70 includes oppositely positioned ends 77, 79. There is no seal at these ends as the bag was 3D printed allowing for continuous manufacture. Mesh bags that are not manufactured by 3D printing would have seals on three of the four corners of the bag. In one embodiment of the 3D printed mesh implant or bag 70, a bottom end 73 of the mesh bag is the only one sealed so that contents do not fall out. In other embodiments, an end 71 is open to allow placement of bone material in the hollow region or compartment 81 of the mesh bag 70. End 71 allows entrance into a hollow region or compartment 81 of the mesh bag 70, where bone material is placed inside of it. The implant is then placed at a bone defect and the mesh bag 70 allows the osteoinductive factors to leave mesh bag 70 and allows influx of bone cells into mesh bag 70. Mesh bag 70 is porous so as to allow influx and efflux of material.

Figure 5B:
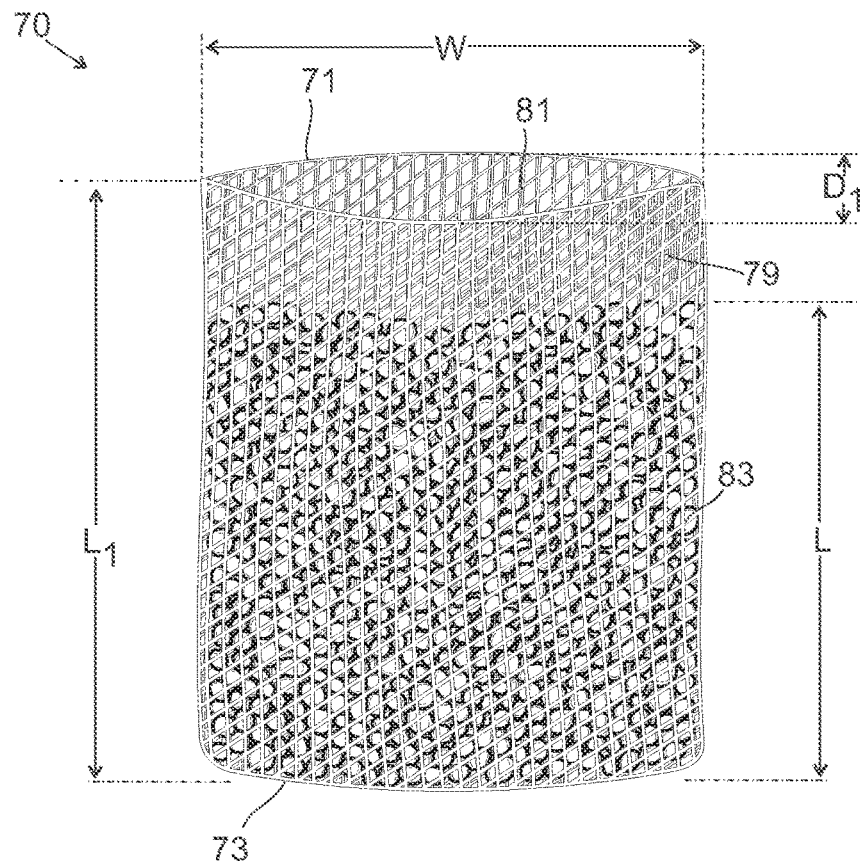
FIG. 5B illustrates a perspective view of a mesh bag as in FIG. 5A containing an osteogenic material in the hollow interior region or compartment.

In FIG. 5B, the hollow region or compartment 81 of the mesh implant is shown having end 71 of mesh bag 70. Mesh bag 70 is filled manually by hand or via an automated process with bone particles 83 (for example, surface demineralized chips and fully demineralized fibers) for use to enhance bone growth.

Figure 5C:
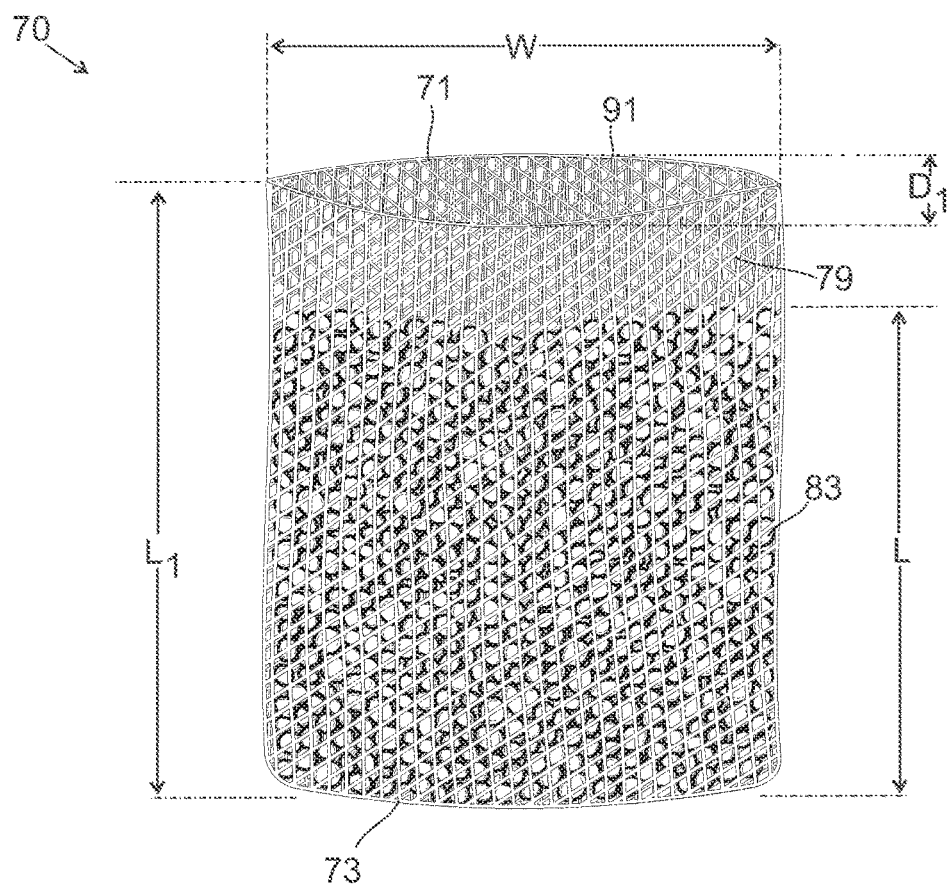
FIG. 5C illustrates a perspective view of a mesh bag as in FIG. 5B containing an osteogenic material in the hollow compartment and having a covering configured for closing the mesh bag.

In FIG. 5C, after the bone material reaches a desired level L, compartment 81 can be enclosed by a covering 91, also generated by 3D printing device 10. In the embodiments illustrated in FIG. 5C, the resulting mesh bags 70 are seamless. In other embodiments, mesh implants or bags 70 generated by 3D printing device 10 can have a seamless cornerless shape. The computer system may have a sensor to determine the proper level of filling of the mesh implants or bags 70 with bone material.

In some embodiments, the dimensions of printing surface 12 allows for printing a mesh implant or bag 70 of different dimensions and shapes that correspond to printing surface 12 (for example, circular, rectangular, square, etc.) The rotation of printing surface 12 shown as B in FIGS. 2 and 3, allows the implant (for example, mesh implant or bag 70) to be printed continuously so that there is a reduced need for sealing the hollow region of the implant. The computer system can calculate the proper volume, length, width, and thickness of the cover to match the volume, length, width, and thickness of the compartment and/or the mesh implant or bag 70.

In some embodiments, mesh implant or bag 70 includes a desired flexibility to allow the mesh implant or bag 70 to be flat, packable and extend between oppositely positioned ends 77 and 79. In some embodiments, mesh implant or bag 70 forms a cylindrical shape between oppositely positioned ends 77 and 79.

Threads 72 may be configured to allow ingrowth of cells while also retaining the osteogenic material within the compartment of mesh implant or bag 70. In some embodiments, print head 30 is configured to extrude threads 72 having a predetermined thickness. In some embodiments, threads 72 have a thickness of about 0.01 mm to about 2.0 mm. In some embodiments, threads 72 have a thickness of about 0.05 mm to about 1.0 mm, or about 0.1 to about 0.5 mm. The thickness of threads 72 may be uniform along the length of each thread 72, or varied across the length of each thread 72. In some embodiments, some threads 72 have a greater thickness than other threads 72 in a mesh implant or bag 70. Threads 72 may be sized to allow for customizable pore sizes between threads 72. In some embodiments, the porous mesh implant or bag 70 is configured to facilitate transfer of substances and/or materials surrounding the surgical site. Upon implantation to a surgical site, mesh implant or bag 70 may participate in, control, or otherwise adjust, or may allow penetration of the mesh implant or bag 70 by surrounding materials, such as cells or tissue.

In various embodiments, mesh implant or bag 70 may be sized according to the needs of a particular application. For example, mesh bag or implant 70 may include dimensions between about 1 mm to about 100 mm in diameter, shown as W in FIG. 5C. In some embodiments, mesh implant or bag 70 includes a diameter (D1 as illustrated in FIG. 5C) of about 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, mesh implant or bag 70 includes a length or depth between about 0.1 cm to about 10 cm, illustrated as L in FIG. 5C. In some embodiments, mesh implant or bag 70 includes a length or depth of about 1 cm, 2 cm, 3 cm, 4 cm, 5 cm, 6 cm, 7 cm, 8 cm, 9 cm, or 10 cm. The desired dimensions can be selected by the user and the computer system can print the implant according to the selection.

In various embodiments, based on the foregoing dimensions, the volume of a 3D printed tubular shaped mesh bag can be easily calculated. For example, in some embodiments, a 3D printed tubular mesh bag having a diameter of 0.5 cm and a length of 0.1 cm would provide a volume of 0.02 cc. In other embodiments, a 3D printed tubular mesh bag having a diameter of 1 cm and a length of 1 cm would provide a volume of 0.79 cc. In yet other embodiments, a 3D printed tubular mesh bag having a diameter of 1.5 cm and length of 3 cm would provide a volume of 5.3 cc.

In some embodiments, threads 72 are extruded onto printing surface 12 in a wave-like configuration having alternating peaks and crests. In some embodiments, printing surface 12 is rotated in alternating clockwise and counter-clockwise directions while material 40 is extruded onto the surface to create sinusoidal shaped waves having evenly shaped curves on the peaks and crests. In some embodiments, the peaks and crests of the waves are pointed to impart variable characteristics to mesh implant or bag 70. In some embodiments, threads 72 are extruded adjacent to one another such that the peaks of a first thread 72 is extruded to contact the crest of an adjacent second thread 72. In some embodiments, the mesh bag 70 may be created entirely from threads 72 having this configuration. Wave-shaped threads 72 impart flexibility and stretchable characteristics onto the manufactured mesh implant or bag 70. The wavelength of the wave-shaped threads 72 may be altered to customize stretchability of mesh implant or bag 70. For example, threads 72 having shorter wavelengths will be able to be stretched more than threads 72 having longer wavelengths. In some embodiments, the stretchability of mesh implant or bag 70 is uniform across its length. In some embodiments, mesh implant or bag 70 includes regions of increased stretchability according to the needs of a surgical application.

The shape, mesh size, thickness, and other structural characteristics, of the mesh implants or bags 70, for example, architecture, may be customized for the desired application. For example, to optimize cell or fluid migration through the mesh, the pore size may be optimized for the viscosity and surface tension of the fluid or the size of the cells. For example, pore sizes between threads 72 on the order of approximately 100-200 μm may be used if cells are to migrate through the mesh. In other embodiments, the wave-shaped threads 72 may be extruded to have larger peaks and crests and the size of the pores may be larger. For example, in some embodiments, the pore size between threads 72 may be about 0.1 mm to about 5 mm, about 0.5 mm to about 3 mm, or about 1 mm to about 2 mm. Mesh size may be controlled by physically weaving strands and by controlling the thickness of threads 72 extruded and sintered on printing surface 12.

In various embodiments, the mesh bag 70 made by 3D printing device 10 may have varying degrees of permeability across its surface. It may be permeable, semi-permeable, or non-permeable. Permeability may be with respect to cells, to liquids, to proteins, to growth factors, to bone morphogenetic proteins, or other. In further embodiments, the material may be braided.

The mesh implant or bag 70 may have any suitable configuration. For example, the mesh implant or bag 70 may be 3D printed onto a printing surface 12 having a variety of shapes, such as, for example, a ring, a cylinder, a cage, a rectangular shape, a suture-like wrap, a continuous tube, or other configurations. Printing surface 12 provides a scaffold onto which mesh implant or bag 70 is 3D printed and from which mesh implant or bag 70 derives its shape. In specific embodiments, the mesh implant or bag 70 may be formed as a thin tube designed to be inserted through catheters or an introducer tube; a rectangular shape designed to fit adjacent to spinal processes for posterolateral spine fusion; a cube; a rectangular prism like structure, as shown in FIG. 4, designed to fit between vertebral bodies or within cages for interbody spinal fusion; a tube-like shape; relatively flat shapes; rectangular shapes; structures pre-shaped to fit around various implants (e.g. dental, doughnut with hole for dental implants); or relatively elastic ring-like structures that will stretch and then conform to shapes (e.g. rubber band fitted around processes). In an embodiment, wherein the mesh implant or bag 70 is formed as a cage, the cage may comprise a plurality of crossed threads 72, which define between them a series of openings for tissue ingrowth. Any of these shapes may be used to contain osteogenic material such as bone material, as discussed herein. Mesh bags 70 may be printed and sintered onto printing surface 12 in such a way as to have one open end, as shown in FIGS. 5A and 5B. In other embodiments, as illustrated in FIG. 5C, mesh implant or bag 70 may be 3D printed and sintered onto printing surface 12 to have open end 71 enclosed by a covering 91 after the interior hollow region or compartment 81 is filled with bone material to a desired level L.

Additionally, the flexible character of the mesh material allows for the mesh implant or bag 70 to be manipulated into a plurality of compartments. For example, in a tubular embodiment, the tube may be formed into a plurality of compartments by tying a cord around the tube at one or more points, or by other suitable mechanism such as crimping, twisting, knotting, stapling, or sewing and also including 3D printing based on a 3D digital model as more particularly described in this application.

A suitable mesh implant or bag 70 that can be made by the 3D printing device of the current application is the MAG-NIFUSE® Bone Graft, available from Medtronic, which comprises surface demineralized bone chips mixed with non-demineralized cortical bone fibers or fully demineralized bone fibers sealed in an absorbable poly(glycolic acid) (PGA) mesh implant or bag or pouch.

In certain embodiments, a bone void can be filled by mesh implant or bag 70 containing bone material. A compartment within mesh implant or bag 70 can be at least partially filled with a bone repair substance. In various embodiments, at least partially filled as used herein, can mean that a percentage of the volume of a compartment or hollow interior region is at least 70% occupied, at least 75% occupied, at least 80% occupied, at least 85% occupied, at least 90% occupied, at least 95% occupied, or 100% occupied. In various embodiments, a sensing means or sensor in communication with the hollow compartment of the mesh implant or bag 70 and also coupled to a computer processor 102 can instruct the processor 102 when a desired percentage volume of the compartment was occupied. Processor 102 can then instruct the 3D printer to generate the covering 91 for enclosing the bone material within the mesh implant or bag 70. Mesh implant or bag 70 can be inserted into an opening in the defect until the defect is substantially filled. In various embodiments, substantially filled, as used herein, can mean that a percentage of the volume of a defect is at least 70% occupied, at least 75% occupied, at least 80% occupied, at least 85% occupied, at least 90% occupied, at least 95% occupied, or 100% occupied.

In some embodiments, mesh implant or bag 70 may be labeled. Such labeling may be done in any suitable manner and at any suitable location on mesh implant or bag 70. In some embodiments, labeling may be done by using a silk screen printing, using an altered weaving or knotting pattern, by using different colored threads 72, or other means. The labeling may indicate information regarding mesh implant or bag 70. Such information might include a part number, donor ID number, number, lettering or wording indicating order of use in the procedure or implant size, etc.

In one embodiment, mesh implant or bag 70 may comprise a penetrable material at a first compartment configured for placement adjacent bone and a substantially impenetrable material at a second compartment configured for placement adjacent soft tissue. For example, the pore size between threads 72 at a first region of mesh implant or bag 70 may be sized large enough to allow cell migration through mesh implant or bag 70, but the pore size between threads 72 at a second region of mesh implant or bag 70 may be sized small enough (or may include a lack of pores altogether) to prevent cell migration. Alternatively, the material of the mesh implant or bag 70 may have a uniform configuration such that adjacent compartments may have substantially identical characteristics. By way of example only, mesh implant or bag 70 may have a porous surface that is positioned adjacent bone, and a separate or opposite surface that has a generally impenetrable surface that is positioned adjacent soft tissue. Alternatively, mesh implant or bag 70 may have one compartment that comprises a porous material, and a second compartment that comprises a substantially impenetrable material.

For either single and multi-compartment mesh implant or bags 70, the mesh implant or bag 70 may be closed after filling substances. Accordingly, mesh implant or bag 70 may be provided in an unfilled, unsealed state immediately following fabrication with 3D printing device 10. After a substance for delivery is placed in mesh implant or bag 70, mesh implant or bag 70 may be permanently or temporarily closed. Permanent closure may be, for example, by 3D printing a covering 91 for enclosing the bone material within the compartment 81 of the mesh implant or bag 70 as illustrated in FIG. 5C. Temporary closure may be by tying, fold lock, cinching, or other means. A temporarily closed mesh implant or bag 70 can be opened without damaging the mesh bag 70 during surgical implantation to add or remove substances in the mesh bag 70.

Suitable adhesives for use for closing the mesh implant or bag 70 may include, for example, cyanoacrylates (such as histoacryl, B Braun, which is n-butyl-2 cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; for example, in some circumstances, a temporary adhesive may be desirable, for example, for fixation during the surgical procedure and for a limited time thereafter, while in other circumstances a permanent adhesive may be desired. Where the compartment is made of a material that is resorbable, the adhesive can be selected that would adhere for about as long as the material is present in the body.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms. In some embodiments, the mesh implant or bag 70 may be attached to a tissue structure through a wrap, a suture, a wire, a string, an elastic band, a cable or a cable tie, or a combination thereof. In some embodiments, the attachment mechanism can be (i) integral to the 3D printed seamless biodegradable mesh implant or bag 70 or (ii) is provided separately from the 3D printed seamless biodegradable mesh implant or bag 70 and can be attached to the 3D printed seamless biodegradable mesh implant or bag 70 for use at an intended graft site.

In some embodiments, mesh implant or bag 70 comprises an extruded material 40 arranged in a mesh configuration. In some embodiments, material 40 of mesh implant or bag 70 is biodegradable. In some embodiments, mesh implant or bag 70 includes only one material which is uniformly extruded to form the entirety of mesh implant or bag 70. In some embodiments, mesh implant or bag 70 comprises a blend of suitable materials 40. In some embodiments, a first group of threads 72 may comprise a first material 40 and a second group of threads 72 comprises a second material 40. In some embodiments, print head 30 is configured to extrude more than one type of material 40. In some embodiments, a first print head 30 is configured to extrude a first material 40 to form threads 72 and a second print head 30 is configured to extrude a second material 40 to form threads 72.

In other embodiments, suitable materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others.

In various embodiments, the material of mesh implant or bag 70 comprises a polymer matrix. In some embodiments, DBM fibers and/or DBM powder are suspended in the polymer matrix to facilitate transfer of cells into and out of the mesh bag to induce bone growth at the surgical site. In other embodiments, mesh implant or bag 70 further comprises mineralized bone fibers suspended in a polymer matrix. In some embodiments, the DBM powder is suspended in the polymer matrix between the DBM fibers and the mineralized bone fibers. In some embodiments, the DBM powder is suspended between the DBM fibers in the polymer matrix so as to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In some embodiments, the polymer matrix comprises a bioerodible, a bioabsorbable, and/or a biodegradable biopolymer that may provide immediate release or sustained release. Examples of suitable sustained release biopolymers include, but are not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers. SAIB (sucrose acetate isobutyrate), or combinations thereof. As persons of ordinary skill in the art are aware, mPEG and/or PEG may be used as a plasticizer for PLGA, but other polymers/excipients may be used to achieve the same effect. mPEG imparts malleability to the polymer in some embodiments, these biopolymers may also be coated on mesh implant or bag 70 to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the mesh implant or bag 70 ranges from about 5 microns to about 250 microns or 5 microns to about 200 microns.

In some embodiments, various components of mesh implant or bag 70 comprise poly(lactide-co-glycolide) (PLGA), polylactide (PLA), polyglycolide (PGA), D-lactide, D,L-lactide, L-lactide. D,L-lactide-co-ε-caprolactone, D,L-lactide-co-glycolide-co-ε-caprolactone, L-lactide-co-ε-caprolactone or a combination thereof.

In some embodiments, material 40 of mesh implant or bag 70 further comprises bone morphogenic proteins (BMPs), growth factors, antibiotics, angiogenesis promoting materials, bioactive agents or other actively releasing materials.

The mesh implant or bag 70 may be used to deliver a substance comprising any suitable biocompatible material. In specific embodiments, mesh implant or bag 70 may be used to deliver surface demineralized bone chips, optionally of a predetermined particle size, demineralized bone fibers, optionally pressed, and/or allograft. For embodiments where the substance is a biologic, the substance may be autogenic, allogenic, xenogenic, or transgenic. Other suitable materials that may be positioned in mesh implant or bag 70 include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above.

In accordance with some embodiments, the material 40 to be positioned in the hollow compartment of the mesh implant or bag 70 may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc, and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants, anti-viral substances such as substances effective against hepatitis; enzyme inhibitors; hormones, neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anticholinergics; anti-glaucoma compounds; anti-parasite and/or anti-protozoal compounds; modulators of cell-extracellular matrix interactions including cell growth inhibitors and antiadhesion molecules; vasodilating agents, inhibitors of DNA, RNA, or protein synthesis; anti-hypertensives; analgesics; anti-pyretics; steroidal and non-steroidal anti-inflammatory agents; anti-angiogenic factors, angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells, DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF), cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc); periodontal ligament chemotactic factor (PDLGF); enamel matrix proteins; growth and differentiation factors (GDF); hedgehog family of proteins; protein receptor molecules; small peptides derived from growth factors above, bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In some embodiments, material 40 may have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

Material 40 may have functional characteristics. Alternatively, other materials 40 having functional characteristics may be incorporated into the mesh implant or bag 70. Functional characteristics may include radiopacity, bacteriocidity, tackiness, source for released materials, etc. Such characteristics may be imparted substantially throughout mesh implant or bag 70 or at only certain positions or portions of mesh implant or bag 70.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form mesh implant or bag 70 and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

In some embodiments, mesh implant or bag 70 may comprise a material that becomes tacky upon wetting. Such material may be, for example, a protein or gelatin based material. Tissue adhesives, including mussel adhesive proteins and cryanocrylates, may be used to impart tackiness to mesh implant or bag 70. In further examples, alginate or chitosan material may be used to impart tackiness to mesh implant or bag 70. In further embodiments, an adhesive substance or material may be placed on a portion of mesh implant or bag 70 or in a particular region of mesh implant or bag 70 to anchor that portion or region of mesh implant or bag 70 in place at an implant site.

Bone Material

In various embodiments, the mesh bags 70 made by 3D printing device 10 include compartments to hold osteogenic material, such as bone material. In various embodiments, the bone material may be particulated such as, for example, in bone chips, powder or fiber form. If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 1000 microns. In some embodiments, the size of the bone powder particles are less than 100 microns. In some embodiments, the size of the bone powder particles are less than 500 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone powder comprises DBM and/or mineralized bone. In some embodiments, the size of the bone powder particles is less than 25 microns. In some embodiments, the bone powder particle size is about 1, 2, 3, 4, 5, 6, 7, 8, 9, 10, 11, 12, 13, 14, 15, 16, 17, 18, 19, 20, 21, 22, 23, 24 and/or 25 microns.

In various embodiments, the bone powder particles and/or the DBM and/or mineralized bone fibers have a sticky outer surface such that the bone powder can adhere to DBM and/or mineralized bone fibers. In various embodiments, the bone particles are naturally sticky. In some embodiments, an adhesive agent is applied to the bone powder and/or the bone fibers comprising a bio-adhesive, glue, cement, cyanoacrylate, silicones, hot melt adhesives and/or cellulosic binders. In various embodiments, the adhesive may be applied to the surface of the bone powder particles by spraying or brushing. In some embodiments, a charge is applied to the fibers and an opposite charge is applied to the bone powder, (i.e, the technique of electrostatic precipitation). The bone powder will be attracted to, and tenaciously adhere to, the surface of the fiber. Any of these application techniques can be repeated one or more times to build up a relatively thick layer of adherent bone powder on the surface of the fibers.

The bone powder can be applied directly to the DBM fiber and/or fully mineralized fiber and the mixture can be disposed in mesh implant or bag 70. In some embodiments, the bone material inserted into a mesh implant or bag 70 contains pores having a pore size from about 0.5 to about 2,000 microns. In some embodiments, bone material inserted into a mesh implant or bag 70 contains pores having a pore size of from about 0.5, 5, 50, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950 to about 2,000 microns. In some embodiments, the pore size of the bone material is uniform. In some embodiments, the pore size of bone material is non-uniform and includes various pore sizes in the range from 0.5 to about 2,000 microns. Alternatively, the DBM fiber, and DBM powder can be placed in a polymer (for example, collagen) and inserted into a porous biodegradable graft body (for example, a pouch, container, mesh implant or bag 70, and the like).

Following shaving, milling or other technique whereby they are obtained, the bone material is subjected to demineralization in order to reduce its inorganic content to a very low level, in some embodiments, to not more than about 5% by weight of residual calcium and to not more than about 1% by weight of residual calcium. Demineralization of the bone material ordinarily results in its contraction to some extent.

Bone used in the methods described herein may be autograft, allograft, or xenograft. In various embodiments, the bone may be cortical bone, cancellous bone, or cortico-cancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone material is immersed in solution to effect its defatting. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The concentration range of the defatting solution is from about 60 to 85 weight percent alcohol or about 70 weight percent alcohol.

Further in accordance with this application, the DBM material can be used immediately for preparation of the implant composition or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPD) fibers DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation vivo by osteoconductive and osteoinductive processes. The osteoinductive effect of implanted DBM compositions is thought to result from the presence of active growth factors present on the isolated collagen-based matrix. These factors include members of the TGF-$\beta$, IGF, and BMP protein families. Particular examples of osteoinductive factors include TGF-$\beta$, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the methods described in this application is prepared from elongated bone fibers which have been subjected to critical point drying. The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1, or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 75:25, 70:30, 60:40, 50:50, 40:60, 30:70, 25:75, 20:80 and/or 10:90. In various embodiments, a surface demineralized chips to fibers ratio is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the mesh implant or bag 70 comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone graft material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM conical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm, 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

To prepare the osteogenic DBM, a quantity of fibers is combined with a biocompatible carrier to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using critical point drying (CD)) technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particular theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Methods of Making

Figure 10:
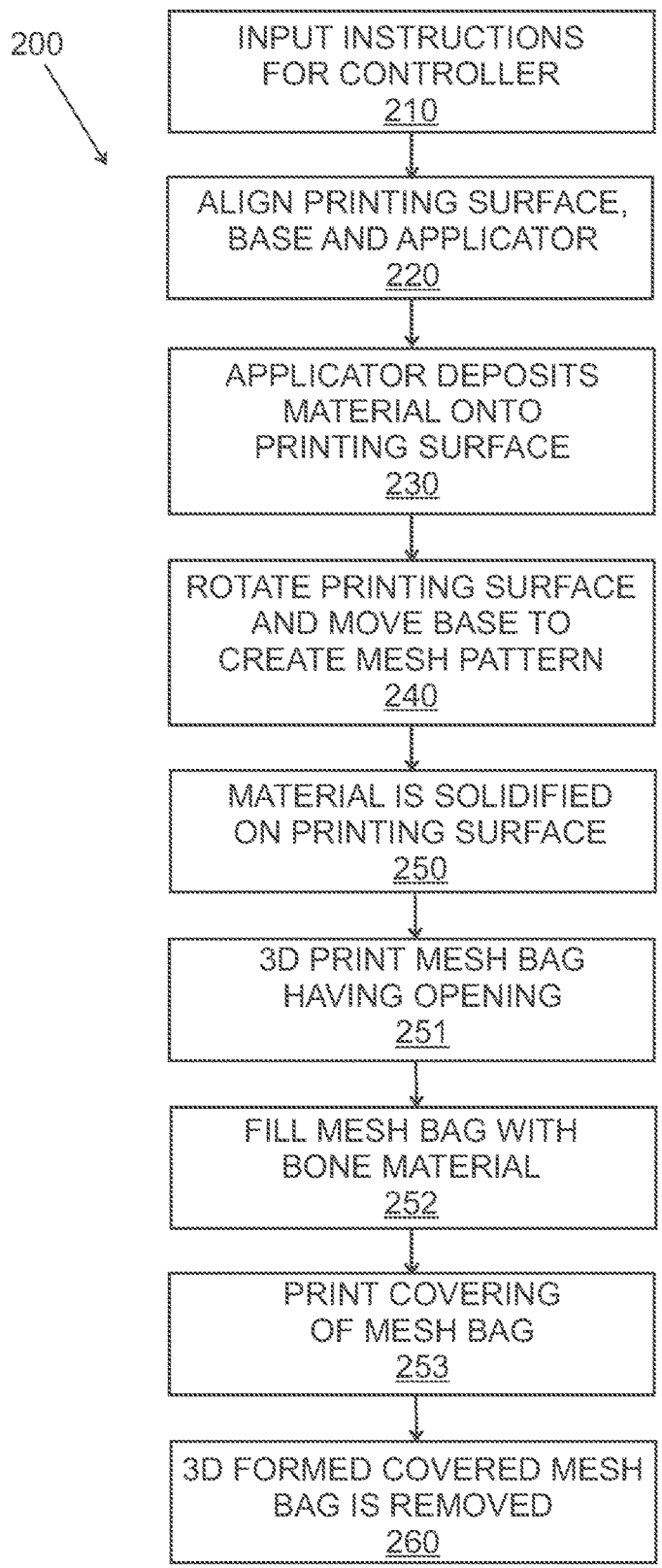
FIG. 10 is a flow diagram illustrating an embodiment of a system for producing a hollow structure, such as a mesh implant or bag, through the use of a 3D printing machine having a rotating printing surface.

In various embodiments as shown in FIG. 10, a computer implemented method 200 of fabricating a hollow structure, such as a mesh implant or bag 70, through use of a 3D printing device 10 is provided. In some embodiments, the method includes step 210 for inputting instructions for a computer processor 102 to carry out the fabrication, step 220 for aligning the printing surface, base and print head relative to one another, step 230 for depositing material onto the printing surface, step 240 for rotating the printing surface and moving the base to create a mesh pattern, and step 250 for solidifying material on the printing surface, step 251 for 3D printing of a mesh implant or bag 70 having a compartment accessible through an opening, step 252 for filling the compartment with bone material, step 253 for 3D printing a covering for enclosing the bone material within the compartment of the mesh implant or bag 70 and step 260 for removing the 3D formed and covered implant or mesh bag 70. In some embodiments, the method comprises: rotating a print surface in alternating clockwise and counterclockwise directions, ejecting material from a print head to the print surface to make a thread having a wave-like pattern with alternating peaks and crests, and rotating the print head such an angular di stance to create a plurality of interconnected threads on the print surface.

In some embodiments, a method for fabricating a hollow structure is provided which includes providing a 3D printing machine 10 having a table 14, a base 16 and a printing surface 12. In various embodiments, printing surface 12 is rotatable about an axis of rotation. Base 16 is configured for planar movement. Printing surface 12 is fixedly disposed with table 14 such that lateral movement of base 16 causes lateral movement of printing surface 12. In some embodiments, base 16 is movable in the x-y plane and is laterally movable in both the x axis and the y axis for precise positioning of printing surface 12. Movement of base 16 allows for positioning of printing surface 12 relative to extension shaft 20 to facilitate depositing materials onto printing surface 12, as discussed herein. 3D printing device 10 further includes a print head 30 to deposit material 40 onto printing surface 12. The deposit material 40 includes material used to make the mesh (e.g., biodegradable polymer, etc.).

In other embodiments, a processor 102 receives instructions for the fabrication of a mesh implant or bag 70. A user may input instructions directly into 3D printing device 10 or may input instructions into an external computer in communication with processor 102. Processor 102 directs movement of base 16, printing surface 12 and print head 30 relative to one another. Processor 102 also directs application of material 40 from print head 30 onto printing surface 12.

According to various aspects, a user loads a material reservoir (not shown) in communication with print head 30 with a suitable material 40. The material may be in powder form, particulate form, gel form, or solid form. Processor 102 moves the printing surface 12 and one or more print heads 30 into place relative to one another. Once positioned, print head 30 begins to deposit material 40 onto printing surface 12. In some embodiments, print head 30 continuously deposits material 40 as printing surface 12 is rotated and/or moved laterally along the x-y plane. In some embodiments, printing surface 12 is rotated in the clockwise and counterclockwise directions while base 16 moves laterally to form wave-shaped threads 72. The degree of rotation may be adjusted to impart flexible and stretchable qualities onto each of the formed threads 72. For example, threads 72 having shorter wavelengths will be able to be stretched more than threads 72 having longer wavelengths. In some embodiments, processor 102 directs rotation of printing surface 12 and lateral movement of base 16 to impart stretchability of mesh implant or bag 70 that is uniform across its length. In some embodiments, processor 102 directs variable rotation of printing surface 12 and lateral movement of base 16 such that mesh implant or bag 70 includes regions of increased stretchability according to the needs of a surgical application.

The movement of base 16, printing surface 12 and print head 30 relative to one another and the application of material 40 onto printing surface 12 is repeated a number of times such that threads 72 encompass the surface of printing surface 12. That is, each time a thread having a wave-like shape is applied to printing surface 12, a similar thread 72 is applied to printing surface 12 adjacent the first thread. In some embodiments, threads 72 are extruded adjacent to one another such that the peaks of a first thread 72 are extruded to contact the crest of an adjacent second thread 72. In some embodiments, the mesh implant or bag 70 may be created entirely from threads 72 having this configuration.

In some embodiments, print head 30 deposits material 40 in powdered form onto printing surface 12. Material 40 must be sintered and/or melted to form threads 72. In some embodiments, a radiation source, such as laser 60 may be used in conjunction with print head 30. Processor 102 directs laser 60 to be focused at a point on which material 40 has been deposited adjacent print head 30. Processor 102 also provides power to laser 60 during desired intervals to prevent unwanted damage to mesh implant or bag 70 and/or printing surface 12 according to the instructions. That is, laser 60 will emit a beam while sintering material 40 to create threads 72, but will not emit a beam when printing surface 12 is being repositioned relative to print head 30. Once all desired sintering has been completed, any excess material 40 may be brushed away from printing surface 12 to be discarded or recycled.

In some embodiments, material 40 may be sintered through use of a heating unit 50 as illustrated in FIG. 1. Heating unit 50 provides energy to printing surface 12 such that powdered material 40 melts and molds together. An amount of heat may be provided such that the material 40 melts quickly upon contact with printing surface 12.

In some embodiments, printing surface 12 is heated or cooled using temperature control unit 50 to remove mesh implant or bag 70. In some embodiments, printing surface 12 may be removed from 3D printing device 10 and submerged in a solvent to loosen and remove mesh implant or bag 70.

Figure 9:
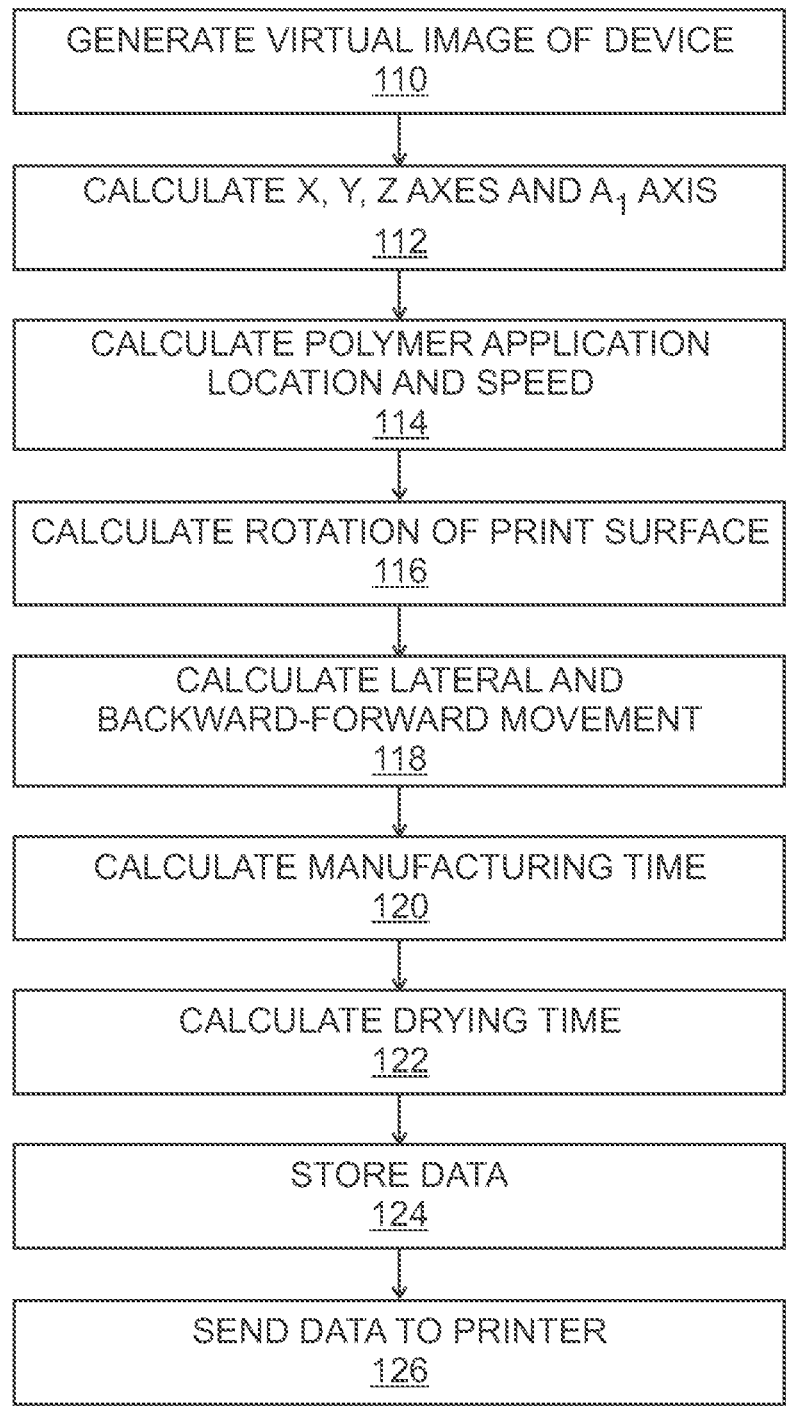
FIG. 9 is a flow diagram illustrating an embodiment of the computer-implemented system for producing a hollow structure, such as a mesh bag.

As shown in FIG. 9, a computer implemented method for producing a hollow structure such as a mesh implant or bag 70 is illustrated. In a first step 110, a user or a designer generates a virtual image of the object or a 3D digital model to be created with the 3D printing machine, such as, for example, mesh implant or bag 70 including a virtual volume of the compartment to enclose the bone material therein and a virtual depth, thickness and volume of the mesh implant or bag 70 and a covering configured for enclosing the compartment of the mesh implant or bag 70. The computer can generate a virtual 3D image of the cover including a virtual volume, length, and width of the covering to be printed. Commercially available CAM software can make the CAD drawing/design of the medical implant into a computer code, (for example, g-code). This code is sent to the device and the controller controls the device and the loading of the print head with the material, the heating and cooling temperature and time of the material, laser emit time, rotation, rotation speed of the print surface, print head, table, lateral movement of the print surface, print head, and table as well as other parameters. The controller device creates a medical implant from or in the material based on the 3D digital model. In some embodiments, the 3D digital model of the mesh implant or bag 70 is generated based on the 3D image of an intended bone repair site. The 3D image of a bone repair site can be obtained by using (i) one or more X-ray images; (ii) a computer aided design (CAD) program, (iii) a cone beam imaging device; (iv) a computed tomography (CT) scan device; (v) a magnetic resonance imaging (MRI), or (vi) 3D laser camera, or a combination thereof.

In a second step 112, processor 102 calculates the X, Y, Z and A1 axes. The device employs Cartesian coordinate system (X, Y, Z) for 3D motion control and employs a 4th axis (A1) for the rotation of the print surface (for example, 360 degrees) relative to the print head 30. The implant can be designed virtually in the computer with a CAD/CAM program, which is on a computer display. The user inputs specific parameters into the computer and then presses print on the display to start the 3D printing manufacturing. The computer logic programs the computer with instructions for loading of print head 30 with material 40; application and thickness of the polymer from print head 30; the heating and cooling temperature and time of the device; laser emit time; rotation, rotation speed of the printing surface 12, print head 30, and/or table 14; and/or lateral movement of the printing surface 12, print head 30, and/or table 14 as well as other parameters in accordance with the received instructions. The controller device causes print head 30 to be located at the appropriate X, Y, Z coordinates for 31) motion control and employs a 4th axis (A1) for the rotation of the print surface (for example, 360 degrees, 180 degrees, 120 degrees) relative to print head 30 to make a medical implant from or in material 40. After the medical implant is produced on all or a portion of printing surface 12, it will have a compartment or a hollow region which typically is greater than the diameter or thickness of the printing surface 12 and can be removed by a tool that engages the printing surface 12. In some embodiments, the device can have a tool to etch, shape, and/or dry the implant before, during or after it is removed from printing surface 12.

In a third step 114, processor 102 calculates the polymer application location and speed by planning coordination of printing surface 12 and print head 30. In some embodiments, the current device does not manufacture the implant device by printing the material in successive layers to form the implant. In a fourth step 116 and a fifth step 118, processor 102 calculates the rotation of printing surface 12 and the lateral and/or backward and forward movement of printing surface 12 and print head 30. In some embodiments, printing surface 12 of the current application has the polymer continuously dispensed from print head 30 and onto printing surface 12 as printing surface 12 rotates in 360 degrees clockwise and/or counterclockwise relative to print head 30 and table 14, and/or printing surface 12 can, in some embodiments, move in a forward, lateral, and/or backward direction so that threads 72 to make the medical implant (for example, a mesh bag or implant 70) are formed in accordance with the instructions received from the computer. In some embodiments, printing surface 12 of the current application has a heat sensitive polymer disposed on it and then print head 30 receives instructions to heat the surface area to be removed (for example, by laser, heating element, or the like). In this way, threads of the polymer are made by removing the heated portions of the polymer and what is left on printing surface 12 are threads 72 for the implant. Printing surface 12 rotates in 360 degrees clockwise and/or counterclockwise relative to print head 30 and table 14, and/or printing surface 12 can, in some embodiments, move in a forward, lateral, and/or backward direction so that threads 72 to make the medical implant (for example, a mesh implant or bag 70) are formed as the rest of the polymer is removed from printing surface 12 in accordance with the instructions received from the computer.

In some embodiments, printing surface 12 of the current application has the polymer in dry powder form continuously dispensed from print head 30 and onto printing surface 12 as printing surface 12 rotates in 360 degrees clockwise and/or counterclockwise relative to print head 30 and table 14, and/or printing surface 12 can, in some embodiments, move in a forward, lateral, and/or backward direction so that the threads to make the medical implant (for example, a mesh implant or bag 70) are formed in accordance with the instructions received from the computer. After, the powder application, which can be from print head 30 from a reservoir therein, print head 30 (for example, a laser or heating element coupled thereto) can heat the powder polymer and form the threads for the medical implant.

Based on the above calculations, processor 102 calculates a projected amount of time it will take to manufacture the medical implant in step 120. In a subsequent step 122, processor 102 calculates the amount of time it will take for the printed medical device to dry. In some embodiments, material 40 applied to printing surface 12 is temperature sensitive and dries and/or cures through heating or cooling. In some embodiments, processor 120 directs a temperature control unit 50 to heat or cool printing surface 12. In some embodiments, processor 120 directs a laser 60 to focus its beam on material 40 applied to printing surface 12 to sinter and cure material 40.

In step 124, the data calculated by processor 102 is stored in memory 100 for subsequent implementation. In some embodiments, processor 102 processes and organizes the calculated data into memory 100. In some embodiments, processor 100 includes value-determining logic, development logic, security logic, and/or analytical logic. In some embodiments, processor 102 updates memory 100 with any new calculation data received from the user. In some embodiments, there is a computer readable storage medium storing instructions that, when executed by a computer, cause the computer to display options for a user to enter, view, and edit some or all features for manufacturing the implant including the loading of print head 30 with material 40; the heating and cooling temperature and time of material 40; laser 60 emit time; rotation angle, rotation speed of printing surface 12, print head 30 and/or print table 14; lateral movement of printing surface 12, print head 30 and table 14; as well as other parameters. The controller device creates a medical implant from or in material 40 by instructions received from the computer. The device employs Cartesian coordinate system (X, Y, Z) for 3D motion control and employs a 4th axis (A1) for the rotation of printing surface 12 (for example, 360 degrees) relative to print head 30.

In a final step 126, the user inputs a command to send the stored data to the printer to create the medical device. The user inputs specific parameters into the computer and then presses print on the display to start the 3D printing manufacturing. The computer logic causes the computer to execute loading of print head 30 with material 40, the heating and cooling temperature and time of the device; laser 60 emit time; rotation; rotation speed of printing surface 12, print head 30, and/or table 14; and/or lateral movement of printing surface 12, print head 30, and/or table 14; as well as other parameters. The controller device causes print head 30 to be located at the appropriate X, Y, Z coordinates for 3D motion control and employs a 4th axis (A1) for the rotation of printing surface 12 (for example, 360 degrees, 180 degrees, 120 degrees) relative to print head 30 to make a medical implant from or in material 40.

Figure 11:
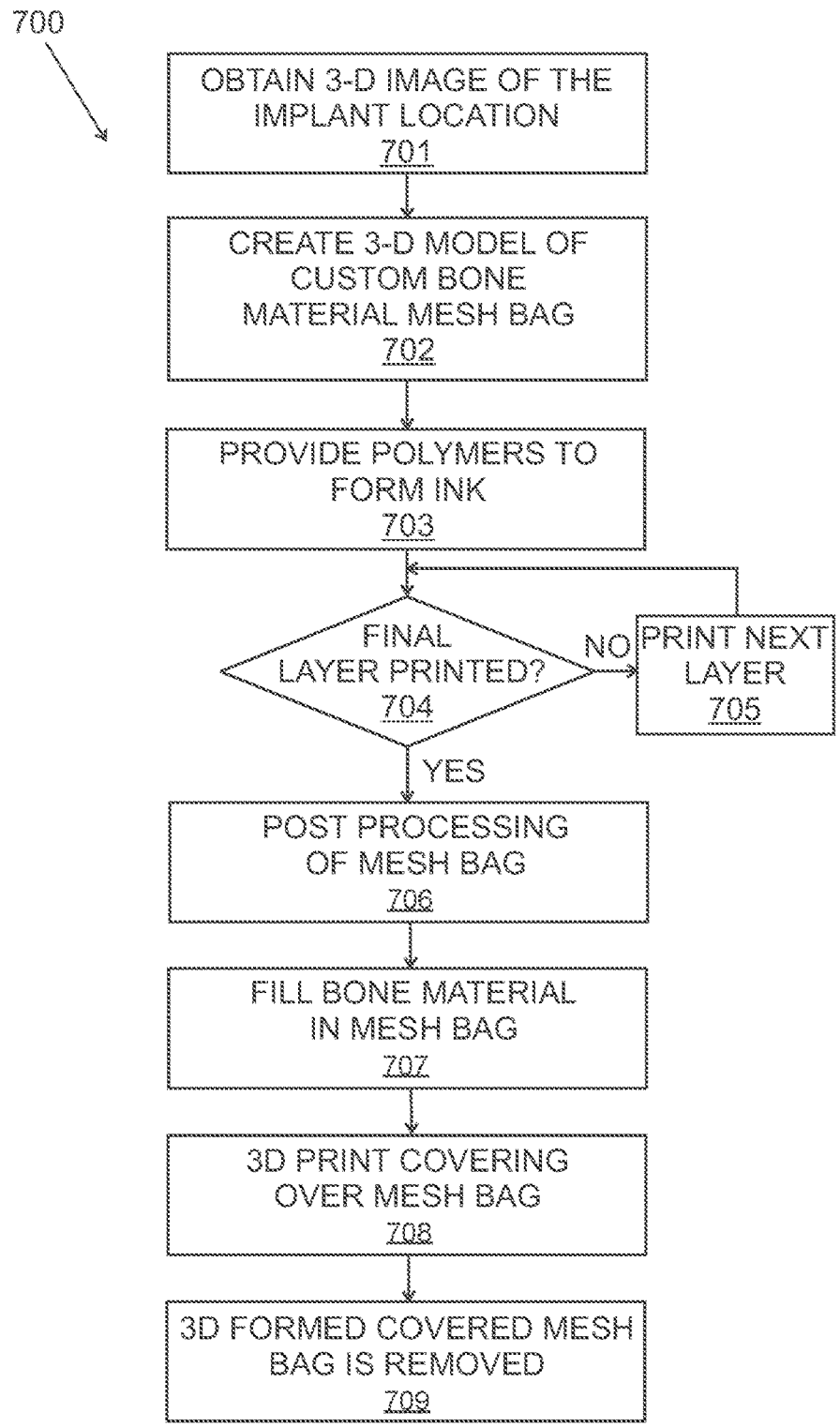
FIG. 11 is a flow diagram illustrating representative steps for producing a mesh implant or bag according to an embodiment of this application.

FIG. 11 is a flow diagram of representative steps of a method 700 of a computer implemented method of producing a mesh implant or bag 70 having a compartment for enclosing a bone material. In various embodiments, the method includes step 701 for obtaining a 3D image of the implant location or bone repair site including the topography of the bone repair site or the implant, or the implant location. Step 701 can be accomplished by using many known techniques of obtaining a 3D image including, but not limited to, (i) one or more X-ray images; (ii) a computer aided design (CAD) program; (iii) a cone beam imaging device; (iv) a computed tomography (CT) scan device; (v) a magnetic resonance imaging (MRI); or a combination thereof. In step 702, the images obtained in step 701, may be input into a suitable digital data processor to create a 3D model of a custom bone material mesh implant or bag 70 which has a compartment to enclose bone material within the mesh implant. In step 703, osteogenic material that preserves the biological activity of demineralized bone particles and/or fibers and has a load bearing structure is supplied to form ink that can be used in steps 704 and 705. In step 704, the 3D printer may first check to determine if the final layer has printed all the layers required to produce the custom mesh implant or bag 70.

These layers may have been provided by a programmed module operative on a digital data processing device, and may be the 3D model of the custom mesh implant or bag 70 reduced to consecutive slices that printed in the correct order may result in the required mesh implant or bag 70.

In step 705, the 3D printer may print the next layer, if the final layer has not yet been printed. This may be done, for instance, by moving the print nozzle in a raster fashion, depositing ink where required. The printing is performed in a sterilized environment.

In step 706, once the 3D printer has printed all the required layers that constitute the custom mesh implant or bag 70, the mesh implant or bag 70 may undergo post print processing. This post processing step may, for instance, include actions such as, but not limited to, dissolving out the sucrose crystals, if any are present, to provide a porous structure and sterilization of the custom bone graft.

In step 707, the 3D printed custom bone mesh implant or bag 70 can be filled with bone material in the hollow compartment present therein up to a desired level as indicated by a sensing device. In step 708, the opening of the mesh implant or bag 70 compartment is enclosed by 3D printing a covering configured for closing the mesh implant or bag 70 compartment. The computer will print the covering based on the 3D digital model generated. It will be configured to cover the mesh implant. The filling step can be done manually or automated.

In step 709, the 3D formed covered mesh implant or bag 70 is removed and may now be inserted into the patient at the intended bone repair site.

Any suitable method may be used for loading a bone material into mesh implant or bag 70. In some embodiments, the bone material may be spooned into mesh implant or bag 70, placed in the mesh implant or bag 70 body using forceps, loaded into mesh implant or bag 70 using a syringe (with or without a needle), or inserted into mesh implant or bag 70 in any other suitable manner including using automation.

For placement, the substance or substances may be provided in mesh implant or bag 70 and placed in vivo, for example, at a bone defect. In one embodiment, mesh implant or bag 70 is placed in vivo by placing mesh implant or bag 70 in a catheter or tubular inserter and delivering mesh implant or bag 70 with the catheter or tubular inserter. Mesh implant or bag 70, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures.

In clinical use, a delivery system comprising a mesh implant or bag 70 and delivered substance may be used in any type of spinal fusion procedure including, for example, posterolateral fusion, interbody fusion (of any type), facet fusion, spinous process fusion, anterior only fusion, or other fusion procedure Examples of such spinal procedures include posterior lumbar interbody fusion (PLIF), anterior lumbar fusion (ALIF) or posterior cervical or cervical interbody fusion approaches. In some embodiments, mesh implant or bag 70 is useful with TLIF, ALIF or XLIF procedures, may be tubular and have dimensions of approximately 2.5 cm in length and approximately 0.5 cm in width. In other ALIF procedures, mesh implant or bag 70 of approximately 1 cm by 1 cm can be used. In various embodiments, mesh implant or bag 70 may be tubular and may have dimensions of approximately 5 mm to approximately 10 mm long and approximately 0.5 cm to 1 cm wide. In other embodiments, mesh implant or bag 70 (with or without substance loaded) may be placed in a cage, for example, for interbody fusion.

In some embodiments, the 3D printed mesh implant or bag 70 may be prefilled with a substance for delivery and other compartments may be empty for filling by the surgeon. In some embodiments, 3D mesh implant or bag 70 comprises a first and a second compartment. In other embodiments, the first and second compartments of 3D mesh implant or bag 70 are in communication with each other. In several embodiments, one compartment may be bone filled while the other compartment of the 3D mesh implant or bag 70 is not. In various embodiments, 3D printed seamless mesh implant or bag 70 conforms to surrounding bony contours when implanted in vivo.

Mesh implant or bag 70 may be used in any suitable application. In some embodiments, mesh implant or bag 70 may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. Mesh implant or bag 70 may be used in a minimally invasive procedure via placement through a small incision, via delivery through a tube, or other means. The size and shape may be designed with restrictions on delivery conditions.

In some embodiments, mesh implant or bag 70 is flexible enough so that it can be folded upon itself before it is implanted at, near, or in the bone defect.

An exemplary application for using a mesh implant or bag 70 as disclosed is fusion of the spine. In clinical use, mesh implant or bag 70 and delivered substance may be used to bridge the gap between the transverse processes of adjacent or sequential vertebral bodies. Mesh implant or bag 70 may be used to bridge two or more spinal motion segments. Mesh implant or bag 70 surrounds the substance to be implanted, and contains the substance to provide a focus for healing activity in the body.

Generally, mesh implant or bag 70 may be applied to a pre-existing defect, to a created channel, or to a modified defect. Thus, for example, a channel may be formed in a bone, or a pre-existing defect may be cut to form a channel, for receipt of mesh implant or bag 70. Mesh implant or bag 70 may be configured to match the channel or defect. In some embodiments, the configuration of mesh implant or bag 70 may be chosen to match the channel. In other embodiments, the channel may be created, or the defect expanded or altered, to reflect a configuration of mesh implant or bag 70. Mesh implant or bag 70 may be placed in the defect or channel and, optionally, coupled using attachment mechanisms.

In various embodiments, a computer system for making a mesh implant or bag 70 having a compartment to enclose a bone material within mesh implant or bag 70 is provided. The computer system comprises logic encoded in the computer for (i) generating a 3D digital model of mesh implant or bag 70 having the compartment, the 3D digital model including a virtual volume of the compartment to enclose the bone material therein and a virtual depth, thickness and volume of mesh implant or bag 70 and a covering configured for closing the compartment of mesh implant or bag 70. (ii) instructing a 3D printer coupled to the computer system to generate mesh implant or bag 70 based on the 3D digital model, (iii) filling the compartment of mesh implant or bag 70 with an amount of the bone material, and (iv) instructing the 3D printer to generate the covering for enclosing the bone material within the compartment of mesh implant or bag 70.

In some embodiments, the computer system for making a mesh implant creates an image of a virtual 3D image of the mesh implant. According to other aspects, the computer system for making a mesh implant comprises a user interface for an authorized user to enter, display, edit, and/or transmit a 3D virtual image of the covered mesh implant.

In many embodiments, the computer system for making a mesh implant or bag 70 comprises at least one sensing means, a memory means, a 3D printer and an input device, each coupled to a processor and to each other, the processor further coupled to a display device for access by an authorized user. In other aspects, the computer system for making a mesh implant or bag 70 of this application provides a seamless and cornerless mesh implant or bag 70.

According to other aspects, the 3D digital model of mesh implant or bag 70 utilized by the computer system is generated based on a 3D image of an intended bone repair site. In some aspects, the 3D printer uses an osteogenic material, the osteogenic material comprising (i) natural mesh materials comprising silk, or extracellular matrix including demineralized bone matrix, ligament, tendon tissue, or silk-elastin, elastin, collagen, cellulose, gelatin, chitosan, alginate, a ceramic with hydroxyapatite; (ii) synthetic polymeric resorbable materials comprising poly(lactic acid) (PLA), poly(glycolic acid) (PGA), poly(lactic acid-glycolic acid) (PLGA), polydioxanone, polyvinyl alcohol (PVA), polyurethanes, polycarbonates, polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, polyglycolide-co-trimethylene carbonate, poly(lactic-co-glycolic acid), or (iii) a polymer comprising polyalkylenes, polyamides, polyesters, poly(glaxanone), poly(orthoesters), poly(pyrolic acid), poly(phosphazenes), or carbon fiber, metal fiber, polyetheretherketones (PEEK), non-resorbable polyurethanes, polyethers, polyethylene terephthalate, polyethylene, polypropylene or Teflon. In several aspects, the computer system also contains logic encoded for the computer to instruct the 3D printer to fill the compartment of mesh implant or bag 70 with bone material which may include (i) fully demineralized bone fibers and surface demineralized bone chips; (ii) the fully demineralized bone fibers and surface demineralized bone chips form a demineralized bone matrix; or (iii) a demineralized bone matrix material comprising fully demineralized bone matrix fibers and surface demineralized bone chips in a ratio of from about 25:75 to about 75:25.

In other embodiments, this application also provides a delivery system comprising a seamless mesh implant or bag 70 having a compartment for enclosing bone material, the seamless mesh implant or bag 70 made by using a 3D printer coupled to a computer, the computer programmed for (i) generating a 3D digital model of mesh implant or bag 70 having the compartment, the 3D digital model including a virtual volume of the compartment to enclose the bone material therein and a virtual depth, thickness and volume of mesh implant or bag 70 and a covering configured for closing the compartment of mesh implant or bag 70, (ii) instructing a 3D printer coupled to the computer system to generate mesh implant or bag 70 based on the 3D digital model, (iii) filling the compartment of mesh implant or bag 70 with an amount of the bone material, and (iv) instructing the 3D printer to generate the covering for enclosing the bone material within the compartment of mesh implant or bag 70. In various aspects, the seamless mesh implant or bag 70 is a biodegradable polymer bag.

Although the invention has been described with reference to preferred embodiments, persons skilled in the art will recognize that changes may be made in form and detail without departing from the spirit and scope of the invention.

What is claimed is:

1. A computer implemented method of producing a mesh implant having a compartment to enclose a bone material within the mesh implant, the method comprising:

generating a 3D digital model of the mesh implant having the compartment, the 3D digital model including a virtual volume of the compartment to enclose the bone material therein and a virtual depth, thickness and volume of the mesh implant;

generating a 3D digital model of a covering configured for closing the compartment of the mesh implant, the 3D digital model including a virtual volume of the covering for closing the compartment of the mesh implant and a virtual depth and thickness of the covering for closing the compartment of the mesh implant;

instructing a 3D printer coupled to a computer to generate the mesh implant based on the 3D digital model of the mesh implant;

filling the compartment of the mesh implant with an amount of the bone material; and instructing the 3D printer to generate the covering based on the 3D digital model of the covering for enclosing the bone material within the compartment of the mesh implant, wherein the mesh implant has a plurality of pores.

2. The computer implemented method according to claim 1, wherein the mesh implant is seamless.

3. The computer implemented method according to claim 1, wherein the 3D digital model of the mesh implant is generated based on a 3D image of an intended bone repair site.

4. The computer implemented method according to claim 3, wherein the 3D image is obtained from (i) one or more X-ray images; (ii) a computer aided design (CAD) program; (iii) a cone beam imaging device; (iv) a computed tomography (CT) scan device; (v) a magnetic resonance imaging (MRI) or a combination thereof.

5. The computer implemented method according to claim 1, wherein the 3D printer uses (i) an osteogenic material that preserves the biological activity of demineralized bone particles and/or fibers, and has a load bearing strength or (ii) the osteogenic material comprises (a) natural mesh materials comprising silk, or extracellular matrix including demineralized bone matrix, ligament, tendon tissue, or silk-elastin, elastin, collagen, cellulose, gelatin, chitosan, alginate, a ceramic with hydroxyapatite, (b) synthetic polymeric resorbable materials comprising poly(lactic acid) (PLA), poly(glycolic acid) (PGA), poly(lactic acid-glycolic acid) (PLGA), polydioxanone, polyvinyl alcohol (PVA), polyurethanes, polycarbonates, polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, polyglycolide-co-trimethylene carbonate, poly(lactic-co-glycolic acid), or (c) a polymer comprising polyalkylenes, polyamides, polyesters, poly(glaxanone), poly(orthoesters), poly(pyrolicacid), poly(phosphazenes), or carbon fiber, metal fiber, polyetheretherketones (PEEK), non-resorbable polyurethanes, polyethers, polyethylene terephthalate, polyethylene, polypropylene or Teflon.

6. The computer implemented method according to claim 1, wherein the bone material comprises autograft, allograft, demineralized bone matrix fiber, demineralized bone chips, demineralized bone powder, or a combination thereof.

7. The computer implemented method according to claim 1, wherein the bone material comprises (i) fully demineralized bone fibers and surface demineralized bone chips; or (ii) fully demineralized bone matrix fibers and surface demineralized bone chips in a ratio of from about 25:75 to about 75:25.

8. The computer implemented method according to claim 1, wherein the mesh implant comprises a bioactive agent, the bioactive agent including protein, carbohydrates, lipids, collagen, allograft bone, autograft bone, tricalcium phosphate, hydroxyapatite, growth and differentiation factors, carriers for growth factors, growth factor extracts of tissues, demineralized bone matrix, bone marrow aspirate, concentrates of lipid derived or marrow derived adult stem cells, umbilical cord derived stem cells, committed or partially committed cells from the osteogenic or chondrogenic lineage, antimicrobials, antibiotics, statins or combinations thereof.

9. The computer implemented method according to claim 1, wherein the mesh implant comprises a first and a second compartment, (i) the first and second compartments are in communication with each other; (ii) one compartment of the 3D printed mesh implant is not filled; or (iii) the 3D printed mesh implant conforms to surrounding bony contours when implanted in vivo.

10. The computer implemented method according to claim 1, wherein the mesh implant comprises a modulus of elasticity of about $1 \times 10^2$ to about $6 \times 10^5$ dynes/cm$^2$ before placement at a bone defect site, and a modulus of elasticity of $1 \times 10^2$ to about $6 \times 10^5$ dynes/cm$^2$ after placement at the bone defect site.

11. A computer system for making a mesh implant having a compartment to enclose a bone material within the mesh implant, the computer system comprising logic encoded in the computer for (i) generating a 3D digital model of the mesh implant having the compartment, the 3D digital model including a virtual volume of the compartment to enclose the bone material therein and a virtual depth, thickness and volume of the mesh implant; (ii) generating a 3D digital model of a covering configured for closing the compartment of the mesh implant, the 3D digital model including a virtual volume of the covering for closing the compartment of the mesh implant and a virtual depth and thickness of the covering for closing the compartment of the mesh implant; (iii) instructing a 3D printer coupled to the computer system to generate the mesh implant based on the 3D digital model of the mesh implant; (iv) filling the compartment of the mesh implant with an amount of the bone material; and (v) instructing the 3D printer to generate the covering based on the 3D digital model of the covering for enclosing the bone material within the compartment of the mesh implant, wherein the mesh implant has a plurality of pores.

12. The computer system according to claim 11, wherein the computer system creates an image of a virtual 3D image of the mesh implant.

13. The computer system according to claim 12, wherein the computer system comprises a user interface for a user to enter, display, edit, and/or transmit the 3D virtual image of the covered mesh implant.

14. The computer system according to claim 11, wherein the computer system comprises at least one sensing means and an input device, each coupled to a processor and to each other, the processor further coupled to a display device for access by an authorized user.

15. The computer system according to claim 11, wherein the mesh implant is seamless.

16. The computer system according to claim 11, wherein the 3D digital model of the mesh implant is generated based on a 3D image of an intended bone repair site.

17. The computer system according to claim 11, wherein the 3D printer contains materials to print the mesh implant including (i) silk, demineralized bone matrix, ligament tissue, tendon tissue, or silk-elastin, elastin, collagen, cellulose, gelatin, chitosan, alginate, a ceramic with hydroxyapatite or a combination thereof; or (ii) synthetic polymeric resorbable materials comprising poly(lactic acid) (PLA), poly(glycolic acid) (PGA), poly(lactic acid-glycolic acid) (PLGA), polydioxanone, polyvinyl alcohol (PVA), polyurethanes, polycarbonates, polyhydroxyalkanoates (polyhydroxybutyrates and polyhydroxyvalerates and copolymers), polysaccharides, polyhydroxyalkanoates, polyglycolide-co-caprolactone, polyethylene oxide, polypropylene oxide, polyglycolide-co-trimethylene carbonate, poly(lactic-co-glycolic acid); or (iii) a polymer comprising polyalkylenes, polyamides, polyesters, poly(glaxanone), poly(orthoesters), poly (pyrolic acid), poly(phosphazenes), or carbon fiber, metal fiber, polyetheretherketones (PEEK), non-resorbable polyurethanes, polyethers, polyethylene terephthalate, polyethylene, polypropylene or Teflon.

18. The computer system according to claim 11, wherein the bone material comprises (i) fully demineralized bone fibers and surface demineralized bone chips; or (ii) fully demineralized bone matrix fibers and surface demineralized bone chips in a ratio of from about 25:75 to about 75:25.

19. A delivery system comprising a seamless mesh implant having a compartment for enclosing bone material, the seamless mesh implant made by using a 3D printer coupled to a computer, the computer programmed for (i) generating a 3D digital model of the mesh implant having the compartment, the 3D digital model including a virtual volume of the compartment to enclose the bone material therein and a virtual depth, thickness and volume of the mesh implant; (ii) generating a 3D digital model of a covering configured for closing the compartment of the mesh implant, the 3D digital model including a virtual volume of the covering for closing the compartment of the mesh implant and a virtual depth and thickness of the covering for closing the compartment of the mesh implant; (iii) instructing a 3D printer coupled to the computer system to generate the mesh implant based on the 3D digital model of the mesh implant; (iv) filling the compartment of the mesh implant with an amount of the bone material; and (v) instructing the 3D printer to generate the covering based on the 3D digital model of the covering for enclosing the bone material within the compartment of the mesh implant, wherein the mesh implant has a plurality of pores.

20. The delivery system according to claim 19, wherein the mesh implant is a biodegradable polymer bag.

\* \* \* \* \*